US010273461B2

United States Patent
Lin

(10) Patent No.: US 10,273,461 B2
(45) Date of Patent: Apr. 30, 2019

(54) EMPLOYING HUMAN ADIPOSE-DERIVED STEM CELLS TO PROPAGATE SERUM-DERIVED HEPATITIS C VIRUS AND USE THEREOF

(71) Applicant: FRONTIER BIO-DRUG DEVELOPMENT LIMITED, Tortola (VG)

(72) Inventor: Chen-Lung Lin, Kaohsiung (TW)

(73) Assignee: FRONTIER BIO-DRUG DEVELOPMENT LIMITED, Tortola (VG)

( * ) Notice: Subject to any disclaimer, the term of this patent is extended or adjusted under 35 U.S.C. 154(b) by 0 days.

(21) Appl. No.: 15/541,913

(22) PCT Filed: Jan. 7, 2015

(86) PCT No.: PCT/CN2015/070243
§ 371 (c)(1),
(2) Date: Jul. 6, 2017

(87) PCT Pub. No.: WO2016/109947
PCT Pub. Date: Jul. 14, 2016

(65) Prior Publication Data
US 2018/0023058 A1  Jan. 25, 2018

(51) Int. Cl.
| C12N 7/00 | (2006.01) |
| G01N 33/576 | (2006.01) |
| C12N 5/0775 | (2010.01) |
| C12Q 1/70 | (2006.01) |
| G01N 33/50 | (2006.01) |

(52) U.S. Cl.
CPC ............ *C12N 7/00* (2013.01); *C12N 5/0667* (2013.01); *C12Q 1/707* (2013.01); *G01N 33/5073* (2013.01); *G01N 33/5767* (2013.01); *C12N 2502/70* (2013.01); *C12N 2770/24251* (2013.01); *C12Q 2600/136* (2013.01); *G01N 2333/186* (2013.01)

(58) Field of Classification Search
None
See application file for complete search history.

(56) References Cited

U.S. PATENT DOCUMENTS

| 5,786,207 A | 7/1998 | Katz et al. |
| 6,391,297 B1 | 5/2002 | Halvorsen |
| 6,777,231 B1 | 8/2004 | Katz et al. |
| 2005/0076396 A1 | 4/2005 | Katz et al. |

FOREIGN PATENT DOCUMENTS

| TW | 200806793 A | 2/2008 |
| WO | 2013/068557 A1 | 5/2013 |

OTHER PUBLICATIONS

Huang, H. J. Human adipose-derived stem cells support complete replication of serum-borne HCV. http://ir.kmu.edu.tw/handle/310902000/35787. 2013.*
Choi et al. (2014) MicroRNA-27a Modulates HCV Infection in Differentiated Hepatocyte-Like Cells from Adipose Tissue-Derived Mesenchymal Stem Cells. PLoS ONE 9(5): e91958. Published on May 13, 2014.*
Choi et al. "MicroRNA-27a Modulates HCV infection in Differentiated Hepatocyte-Like Cells from Adipose Tissue-Derived Mesenchymal Stem Cells", *PLOS ONE* 9(5);e91958 (2014) 9 pages.
Huang "Human adipose-derived stem cells support complete replication of serum-borne HCV", *Kaohsiung Medical University Institutional Respository* (2013) 2 pages.
Wu et al. "Productive Hepatitis C Virus Infection of Stem Cell-Derived Hepatocytes revels a Critical Translation to Viral Permissiveness during Differentiation", *PLoS Pathogens* 8(4):e1002617 (2012) 14 pages.
Notification of Transmittal of the International Search Report and the Written Opinion of the International Searching Authority, or the Declaration corresponding to International Application No. PCT/CN2015/070243 dated Sep. 2, 2015.

(Continued)

*Primary Examiner* — Nianxiang Zou
(74) *Attorney, Agent, or Firm* — Myers Bigel, P.A.

(57) ABSTRACT

Hepatitis C virus replication at extrahepatic sites has been suggested; however, complete viral replication has only been confirmed in hepatocytes. Here we show that human adipogenic DLK-1+ stem cells (hADSC) freshly isolated from HCV-infected individuals contained viral transcripts, replication intermediates and viral antigens in vivo, and viral transcripts increased in supernatants upon prolonged ex vivo culture. Furthermore, naive hADSC isolated from HCV (−) individuals support complete replication of clinical isolates in vitro, and the infection is donor-nonspecific for cells and cross-genotypic for viruses. Viral infection/replication is mediated through CD81, LDL-R, SR-B1, EGFR, Apolipoprotein E, occludin, claudin-1, NPC1L1 and diacylglycerol acetyltransferase-1, and can be inhibited by anti-viral drugs. In addition, the physical properties of hADSC-propagated viral particles resemble clinical isolates more than JFH1/HCVcc, and viruses propagated by in vitro infected hADSC are infectious to primary human hepatocytes. Therefore, hADSC are an in vivo HCV reservoir and represent a novel venue of clinical virus-host interaction. hADSC can also be exploited as a physiologically relevant primary cell culture system to propagate clinical isolates.

18 Claims, 24 Drawing Sheets

(56) References Cited

OTHER PUBLICATIONS

Huang Hsin-Jui "Human adipose-derived stem cells support complete replication of serum-borne HCV", Kaohsiung Medical University Medical Research Institute Dissertation pp. 1-50 (2013) (Abstract Only).
Hsieh et al. "The Genotype of Hepatitis C Virus Has Important Clinical and Therapeutic Implications", [J]. Internal Medicine 20(4:309-319 (2009) (Abstract Only).
Office Action corresponding to Taiwan Application No. 104115953 dated Oct. 5, 2017.
Arrigoni et al. "Isolation characterization and osteogenic differentiation of adipose-derived stem cells: from small to large animal models", *Cell Tissue Res* 338:401-411 (2009).
Bartenschlager et al. "Novel Insights into Hepatitis C Virus Replication and Persistence", *Advances in Virus Research* 63:71-180 (2004).
Bunnell et al. "Adipose-derived stem cells: isolation, expansion and differentiation", *Methods* 45:115-120 (2008).
Erickson et al. "Chondrogenic Potential of Adipose Tissue-Derived Stromal Cells in Vitro and in Vivo", *Biochem Biophys Res Commun* 290:763-769 (2002).
Gondeau et al. "In vitro infection of primary human hepatocytes by HCV-positive sera: Insights on a highly relevant model", *Gut* 63:1490-1500 (2014).
Halvorsen et al. "Thiazolidinediones and Glucocorticoids Synergistically Induce Differentiation of Human Adipose Tissue Stromal Cells: Biochemical, Cellular, and Molecular Analysis", *Metabolism* 50(4):407-413 (2001).
Halvorsen et al. "Extracellular Matrix Mineralization and Osteoblast Gene Expression by Human Adipose Tissue-Derived Stromal Cells", *Tissue Eng* 7(6):729-741 (2001).
Harp et al. "Differential Expression of Signal Transducers and Activators of Transcription during Human Adiodgenesis", *Biochem Biophys Res Commun* 281:907-912 (2010).
Hauner et al. "Glucocorticoids and Insulin Promote the Differentiation of Human Adipocyte Precursor Cells into Fat Cells", *J. Clinical Endocrinology and Metabolism* 64(4):832-835 (1987).
Kanto et al. "Buoyant Density of Hepatitis C Virus Recovered from Infected Hosts: Two Different Features in Sucrose Equilibrium Density-gradient Centrifugation Related to Degree of Liver Inflammation", *Hepatology* 19:296-302 (1994).
Katz et al. "Emerging Approaches to the Tissue Engineering of Fat", *Clinics in Plastic Surgery* 26(4):587-603 (1999).
Khatri et al. "Influenza virus Infects Bone Marrow Mesenchymal Stromal Cells in Vitro: Implications for Bone Marrow Transplantation", *Cell Transplantation* 22(3):461-468 (2013) (17 pages).
Lohmann et al. "On the History of Hepatitis C Virus Cell Culture Systems", *J. Med. Chem.* 57:1627-1642 (2014).
Oertel et al. "Purification of Fetal Liver Stem/Progenitor Cells Containing all the Repopulation Potential for Normal Adult Rat Liver", *Gastroenterology* 134:823-832 (2008).
Okamoto et al. "Typing hepatitis C virus by polymerase chain reaction with type-specific primers: application to clinical surveys and tracing infectious sources", *J. General Virology* 73:673-679 (1992).
Royer et al. "A study of susceptibility of primary human Kupffer cells to hepatitis C virus", *J. Hepatology* 38:250-256 (2003).
Smas et al. "Pre-1, a Protein Containing EGF-like Repeats, Inhibits Adipocyte Differentiation", *Cell* 73:725-734 (1993).
Burris et al. "A Novel Method for Analysis of Nuclear Receptor Function at Natural Promoters: Peroxisome Proliferator-Activated Receptor γ Agonist Actions on aP2 Gene Expression Detected Using Branched DNA Messenger RNA Quantitation", *Mol Endocrinol* 13:410-417 (1999).
Gronthos et al. "Surface Protein Characterization of Human Adipose Tissue-Derived Stromal Cells", *J. Cellular Physiology* 189:54-63 (2001).
Saladin et al. "Differential Regulation of Peroxisome Proliferator Activated Receptor (PPARγ1) and PPARγ2)Messenger RNA Expression in the Early Stages of Adipogenesis", *Cell Growth and Differentiation* 10:43-48 (1999).
Sen et al. "Adipogenic Potential of Human Adipose Derived Stromal Cells from Multiple Donors is Heterogeneous", *J. Cellular Biochemistry* 81:312-319 (2001).
Zhou et al. "Analysis of the pattern of gene expression during human adipogenesis by DNA microarray", *Biotechnol. Techniques* 13:513-517 (1999).
Zuk et al. "Multilineage Cells from Human Adipose Tissue: Implications for Cell-Based Therapies", *Tissue Eng.* 7(2):211-228 (2001).
Zuk et al. "Human Adipose Tissue is a Source of Multipotent Stem Cells", *Molecular Biology of the Cell* 13:4279-4295 (2002).
Musina et al. "Comparison of Mesenchymal Stem Cells Obtained from Different Human Tissues", *Cell Technologies in Biology and Medicine* 1(2):504-509 (2005).
Romanov et al. "Mesenchymal Stem Cells from Human Bone Marrow and Adipose Tissue: Isolation, Characterization, and Differentiation Potentialities", *Cell Technologies in Biology and Medicine* 3:138-143 (2005).
Zannettino et al. "Multipotential Human Adipose-Derived Stromal Stem Cells Exhibit a Perivascular Phenotype In Vitro and In Vivo", *J. Cellular Physiology* 214:413-421 (2008).
Lindenbach et al. "Unravelling hepatitis C virus replication from genome to function", *Nature* 436:933-938 (2005).
Scheel et al. "Understanding the hepatitis C virus life cycle paves the way for highly effective therapies", *Nature Medicine* 19(7):837-849 (2013).
Blackard et al. "Extrahepatic Replication of HCV: Insights into Clinical Manifestations and Biological Consequences", *Hepatology* 44:15-22 (2006).
Laporte et al. "Differential distribution and internal translation efficiency of hepatitis C virus quasispecies present in dendritic and liver cells", *Blood* 101:52-57 (2003).
Wilkinson et al. "Hepatitis C Virus Neuroinvasion: Identification of Infected Cells", *J. Virology* 83(3):1312-1319 (2009).
Letendre et al. "Pathogenesis of Hepatitis C Virus Coinfection in the Brains of Patients Infected with HIV", *J. Infect. Diseases* 196:361-370 (2007).
Yang et al. "Complete replication of hepatitis B virus and hepatitis C virus in a newly developed hepatoma cell line", *PNAS* 111:1264-1273 (2014).
Abdallah et al. "Regulation of Human Skeletal Stem Cells Differentiation by Dlk1/Pref-1", *J. Bone and Mineral Research* 19(5):841-852 (2004).
Yoshimura et al. "Characterization of Freshly Isolated and Cultured Cells Derived from the Fatty and Fluid Portions of Liposuction Aspirates", *J. Cellular Physiology* 208:64-76 (2006).
Lin et al. "Engineered Adipose Tissue of Predefined Shape and Dimensions from Human Adipose-Derived Mesenchymal Stem Cells", *Tissue Eng.: Part A* 14(5):571-581 (2008).
Jammart et al. "Very-Low-Density Lipoprotein (VLDL)-Producing and Hepatitis C Virus-Replicating HepG2 Cells Secrete No More Lipoviroparticles than VLDL-Deficient Huh7.5 Cells", *J. Virology* 87(9):5065-5080 (2013).
Owen et al. "Apolipoprotein E on hepatitis C virion facilitates infection through interaction with low-density lipoprotein receptor", *Virology* 394:99-108 (2009).
Sainz, Jr. et al. "Identification of the Niemann-Pick C1-like 1 cholesterol absorption receptor as a new hepatitis C virus entry factor", *Nature Medicine* 18(2):281-285 (2012).
Dorner et al. "A genetically humanized mouse model for hepatitis C virus infection", *Nature* 474(9):208-211 (2011).
Krapivner et al. "DGAT1 Participates in the Effect of HNF4A on Hepatic Secretion of Triglyceride-Rich Lipoproteins", *Arterioscler Thromb Vasc Biol.* 30:962-967 (2010).
Herker et al. "Efficient hepatitis C virus particle formation requires diacylglycerol acyltransferase-1", *Nature Medicine* 16(11):1295-1298 (2010).
Kaul et al. "Essential Role of Cyclophilin A for Hepatitis C Virus Replication and Virus Production and Possible Link to Polyprotein Cleavage Kinetics", *PLoS Pathog* 5(8):e1000546 (2009).

(56) References Cited

OTHER PUBLICATIONS

Lee et al. "Inhibition of adipogenesis and development of glucose intolerance by soluble preadipocyte factor-1 (Pref-1)", *J. Clin. Invest.* 111(4):453-461 (2003).
Gesta et al. "Developmental Origin of Fat: Tracking Obesity to Its Source", *Cell* 131:242-256 (2007).
Wang et al. "Pref-1 Regulates Mesenchymal Cell Commitment and Differentiation Sox9", *Cell Metabolism* 9:287-302 (2009).
Gimble et al. "Adipose-Derived Stem Cells for Regenerative Medicine", *Circ. Res.* 100:1249-1260 (2007).
Mizuno et al. "Concise Review: Adipose-Derived Stem Cells as a Novel Tool for Future Regenerative Medicine", *Stem Cells* 30:804-810 (2012).
Parsons et al. "Susceptibility of human fetal mesenchymal stem cells to Kaposi sarcoma-associated herpesvirus", *Blood* 104(9):2736-2738 (2004).
Avanzi et al. "Susceptibility of Human Placenta Derived Mesenchymal Stromal/Stem Cells to Human Herpesvirus Infection", *PLOS ONE* 8(8):e71412 (2013).
Soland et al. "Perivascular Stromal Cells as a Potential Reservoir of Human Cytomegalovirus", *American Journal of Transplantation* 14:820-830 (2014).
Gibellini et al. "HIV-1 and recombinant gp120 affect the survival and differentiation of human vessel wall-derived mesenchymal stem cells", *Retrovirology* 8:40 (2011) (18 pages).
Ma et al. "Hepatitis B virus infection and replication in human bone marrow mesenchymal stem cells", *Virology Journal* 8:486 (2011) (8 pages).
Rodbell et al. "Metabolism of Isolated Fat Cells. II. The Similar Effects of Phospholipase C (*Clostridium perfringens* α Toxin) and of Insulin on Glucose and Amino Acid Metabolism", *J. Biological Chemistry* 241(1):130-139 (1966).
Eto et al. "Characterization of Structure and Cellular Components of Aspirated and Excised Adipose Tissue", *Plastic and Regonstructive Surgery* 124(4):1087-1097 (2009).
Bukh et al. "Importance of primer selection for the detection of hepatitis C virus RNA with the polymerase chain reaction assay", *Proc. Natl. Acad. Sci. USA* 89:187-191 (1992).
Shimizu et al. Hepatitis C Virus: Detection of intracellular Virus Particles by Electron Microscopy, *Hepatology* 23:205-209 (1996).
Toniutto et al. "Discordant Results from Hepatitis C Virus Genotyping by Procedures Based on Amplification of Different Genomic Regions", *J. Clinical Microbiology* 34(10):2382-2385 (1996).
Jopling et al. "Modulation of Hepatitis C Virus RNA Abundance by a Liver-Specific MicroRNA", *Science* 309:1577-1581 (2005).
Al-Sadi et al. "Occludin regulates macromolecule flux across the intestinal epithelial tight junction barrier", *Am. J. Physiol. Gastrointest. Liver Physiol.* 300LG1054-G1064 (2011).

Jiang et al. "Hepatitis C Virus Attachment Mediated by Apoliloprotein E binding to Cell Surface Heparan Sulfate", *J. Virology* 86(13):7256-7267 (2012).
Kato et al. "Cell culture and infection system for hepatitis C virus", *Nature Protocols* 1(5):2334-2339 (2006).
Lindenbach et al. "Complete Replication of Hepatitis C Virus in Cell Culture", *Science* 309:623-626 (2005).
Lindenbach et al. "Cell culture-grown hepatitis C virus is infectious in vivo and can be recultured in vitro", *PNAS* 103(10):3805-3809 (2006).
Bhogal et al. "Isolation of Primary Human Hepatocytes from Normal and Diseased Liver Tissue: A One Hundred Liver Experience", *PLoS ONE* 6(3):e18222 (2011).
Clark et al. "Nonalcoholic fatty liver disease", *Gastroenterology* 122:1649-1657 (2002).
Negro "Mechanisms and significance of liver steatosis in hepatitis C virus infection", *World J. Gastroenterol* 12(42):6756-6765 (2006).
Adinolfi et al. "Steatosis Accelerates the Progression of Liver Damage of Chronic Hepatitis C Patients and Correlates with Specific HCV Genotype and Visceral Obesity", *Hepatology* 33:1358-1364 (2001).
Kapadia et al. "Hepatitis C virus RNA replication is regulated by host geranylgeranylation and fatty acids", *PNAS* 102(7):2561-2566 (2005).
Mankouri et al. "Enhanced hepatitis C virus genome replication and lipid accumulation mediated by inhibition of AMP-activated protein kinase", *PNAS* 107(25):11549-11554 (2010).
Olson et al. "PDGFRβ Signaling Regulates Mural Cell Plasticity and Inhibits Fat Development", *Developmental Cell* 20:815-826 (2011).
Plieri et al. "Binding of Hepatitis C Virus to CD81", *Science* 282:938-941 (1998).
Molina et al. "Serum-Derived Hepatitis C Virus Infection of Primary Human Hepatocytes is Testraspanin CD81 Dependent", *J. Virology* 82(1):569-574 (2007).
Ploss et al. "Human ccluding is a hepatitis C virus entry factor required for infection of mouse cells", *Nature* 457:882-886 (2009).
Evans et al. "Claudin-1 is a hepatitis C virus co-receptor required for a late step in entry", *Nature* 446:801-805 (2007).
Liu et al. "Human Apolipoprotein E Peptides Inhibit Hepatitis C Virus Entry by Blocking Virus Binding", *Hepatology* 56:484-491 (2012).
Lupberger et al. "EGFR and EphA2 are host factors for hepatitis C virus entry and possible targets for antiviral therpy", *Nature Medicine* 17(5):589-595 (2011).
Delany et al. "Proteomic Analysis of Primary Cultures of Human Adipose-derived Stem Cells", Molecular & Cellular Proteomics 4(6):731-740 (2005).
Extended European Search Report corresponding to European Application No. 15876456.3 dated May 2, 2018.

\* cited by examiner

A.

B.

C.

D.

E.

F.

A.

B.

C.

D.

E.

F.

A.

B.

C.

D.

E.

F.

G.

H.

I.

A.

B.

C.

D.

E.

1. Naive Huh7.5 culture supernatant
2. HCVcc infected Huh7.5 culture supernatant
3. 21 days' supernatant of HCVcc infected hADSC
4. 21 days' supernatants of HCVser infected hADSC

F.

1: infected by 21 days' supernatant of hADSC exposed to HCV(-) control serum
2: infected by 21 days' supernatant of hADSC exposed to HCVser-1b
3: infected by 21 days' supernatant of hADSC exposed to HCVser-2b

G.

A.

B.

A.

B.

C.

A.

B

C

A.

EMPLOYING HUMAN ADIPOSE-DERIVED STEM CELLS TO PROPAGATE SERUM-DERIVED HEPATITIS C VIRUS AND USE THEREOF

RELATED APPLICATIONS

This application is a 35 U.S.C. § 371 national phase application of and claims priority PCT Application PCT/CN2015/070243 filed Jan. 7, 2015, the entire content of which is incorporated herein by reference in its entirety.

FIELD OF THE INVENTION

The present invention relates to systems and methods for propagating hepatitis C virus (HCV), and use thereof.

BACKGROUND OF THE INVENTION

HCV is an enveloped positive-strand RNA virus in the Flaviviridae family. It contains a 9.6 kb genome starting at an untranslated region (5'-UTR), followed by sequences encoding structural proteins (core, E1, and E2) and non-structural (NS) proteins including p7, NS2, NS3, NS4 and NS5 (for review, see reference[1,2]). Unlike infection of hepatitis B virus (HBV), HCV infection is a multifaceted disease with both hepatic and extrahepatic manifestations[3], and HCV can reside at non-hepatic cells[4-6], which may play a role in viral persistence and reactivation. However, in vitro systems to investigate the extrahepatic replication of HCV have been severely limited. In terms of primary cells, direct infection of serum-borne HCV (HCVser) has been demonstrated only in human and chimpanzee hepatocytes, which are difficult to maintain in culture and also have significant donor-to-donor variations in cell properties. Furthermore, most in vitro cell culture methods employ molecular clones, not the natural virus (for review, see reference[7]). These models also grow viruses in non-primary cells, including the HLZ01 hepatoma cell line recently reported to support infection of clinical HCV isolates[8]. Therefore, how far the data can be extrapolated to the actual clinical virus-host interaction remains a concern.

Thus, there is still a need for alternative systems and methods of propagating serum-borne hepatitis C virus (HCV).

SUMMARY OF THE INVENTION

This Summary is provided to present a summary of the invention to briefly indicate the nature and substance of the invention. It is submitted with the understanding that it will not be used to interpret or limit the scope or meaning of the claims.

In one aspect, the present disclosure provides a human adipose-derived stem cells (hADSCs)-based system for propagating hepatitis C virus (HCV), which comprises hADSCs, culture medium suitable for culturing hADSCs, and HCV. In some embodiments, the hADSCs are primary cells or passaged cells, preferably the passage 1-15 cells, more preferably the passage 1-6 cells. In some embodiments, the hADSCs are positive for a specific marker DLK-1 (i.e., Pref-1). In some embodiments, the HCV is derived from blood, serum, plasma or body fluid of an individual infected with HCV, or is a clinical HCV isolate. In some embodiments, the HCV is of genotype selected from the group consisting of 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, and any combination thereof, preferably genotype 1a, 1b, 2a, 2b, or mixed 2a+2b. In some embodiments, the system supports complete replication of HCV, including the production of infectious virus.

In another aspect, the present disclosure provides a method for propagating hepatitis C virus (HCV), comprising using hADSCs to propagate HCV in culture medium suitable for culturing hADSCs under a condition suitable for replication of HCV. In some embodiments, the hADSCs are primary cells or passaged cells, preferably the passage 1-15 cells, more preferably the passage 1-6 cells. In some embodiments, the hADSCs are positive for a specific marker DLK-1 (i.e., Pref-1). In some embodiments, the HCV is derived from blood, serum, plasma or body fluid of an individual infected with HCV, or is a clinical HCV isolate. In some embodiments, the HCV is of genotype selected from the group consisting of 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, and any combination thereof, preferably genotype 1a, 1b, 2a, 2b, or mixed 2a+2b. In some embodiments, the method supports complete replication of HCV.

In another aspect, the present disclosure provides the use of hADSCs for propagating HCV, or conducting HCV life cycle analyses, or diagnosing HCV infections, or screening of anti-viral compounds, or characterizing HCV of a subject infected with such HCV.

In another aspect, the present disclosure provides the use of hADSCs in the manufacture of a kit for diagnosing HCV infections, or propagating HCV, or conducting HCV life cycle analyses, or screening of anti-viral compounds, or characterizing HCV of a subject infected with such HCV.

In another aspect, the present disclosure provides a method for diagnosing an HCV infection in a subject comprising the steps of:

a) providing hADSCs, b) incubating the hADSCs with a biological sample obtained from the subject in a culture medium suitable for culturing hADSCs, c) culturing said hADSCs for a time sufficient for permitting HCV replication, and d) detecting the level of HCV replication, wherein the detection of an HCV replication is indicative that said subject is infected with HCV.

In some embodiments, said biological sample is derived from blood, serum, plasma or body fluid.

In another aspect, the present disclosure provides a method for screening an anti-HCV compound, comprising the steps of:

a). contacting hADSCs in a culture medium in a first container with HCV in the absence of a candidate compound;

b). determining the level of HCV in the culture medium in the first container in the absence of the candidate compound;

c). contacting hADSCs in a culture medium in a second container with HCV in the presence of the candidate compound;

d). determining the level of HCV in the culture medium in the second container in the presence of the candidate compound;

e). comparing the level of HCV in the presence of the candidate compound with the level of HCV in the absence of the candidate compound; and f). identifying the candidate compound as an anti-HCV compound when the level of HCV in the presence of the candidate compound is lower than level of HCV in the absence of the candidate compound.

In some embodiments, the level of HCV is determined by measuring an HCV titre, the level of an HCV nucleic acid, or the level of an HCV polypeptide.

In some embodiments, the candidate compound is at least one selected from the group consisting of: a chemical compound, a protein, a peptide, a peptidomemetic, an antibody, a nucleic acid, an antisense nucleic acid, an shRNA, a ribozyme, and a small molecule chemical compound.

In some embodiments, the HCV is at least one of the HCV genotypes selected from the group consisting of genotype 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, and any combination thereof, preferably genotype 1a, 1b, 2a, 2b, and mixed 2a+2b.

Other aspects are described infra.

BRIEF DESCRIPTION OF THE DRAWINGS

The foregoing summary and following detailed description are better understood when read in conjunction with the accompanying drawings which are included by way of example and not by way of limitation.

Note: Historically it has been difficult to detect HCV antigens in the infected liver tissue. However, staining of isolated cells does not appear to be so non-specific as staining on liver tissues, as long as the time for color development is well controlled (see "Methods").

Figure 8:
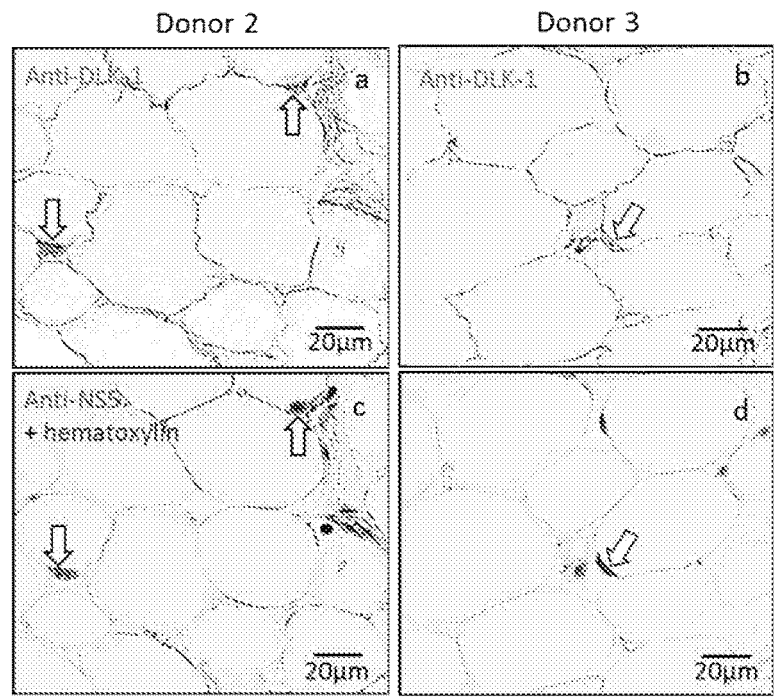

FIG. 8. DLK-1[+] cells in adipose tissues of HCV-infected individuals co-expressed HCV NS5 antigen. Fatty tissues were harvested from HCV-infected individuals (Table 1), and immunostained with anti-DLK-1 Ab (red label, white arrows, panels a & b), followed by anti-NS5 Ab (brown label, white arrows, panels c & d) and hematoxylin (blue label in panels c & d) on the same sections, as described in Method. In all sections of HCV(+) fatty tissues examined, about 0-4 DLK-1[+]NS5[+] cells could be detected in a high-power field (400×). Panels a & c were from donor 2 and panels b & d were from donor 3. Images of staining with isotype control antibody were similar to those presented in FIG. 1E.

Figure 9:
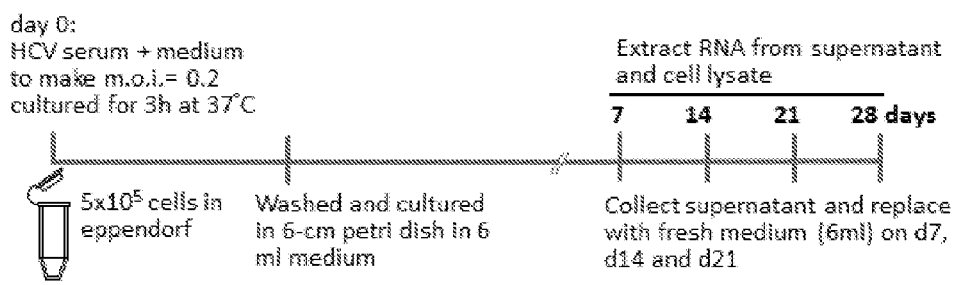

FIG. 9. Protocol for infecting hADSC in suspension. hADSC were prepared from HCV(−) individuals and passaged in culture as described[12-13]. Passage-2 to -6 hADSC were exposed to HCVser (Table 2) at 0.2 moi ($1 \times 10^5$ HCV 5′-UTR copy number versus $5 \times 10^5$ hADSC cells), adjusted by diluting the HCV(+) serum with fresh medium. After 3 h, cells were washed with PBS for 5 times and subsequently cultured in 6-ml fresh medium. Supernatants and cell lysates were harvested on day 7, 14, 21 and 28, and RNAs were extracted for RT-PCR of 5′-UTR.

Figure 10:
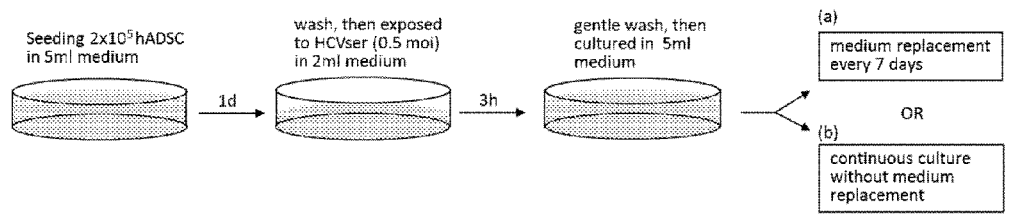

FIG. 10. Infection of hADSC adherent on plastics with HCVser. hADSC were plated in 6-cm petri dishes for 1 day to allow cell attachment. HCVser was subsequently added in a final volume of 2 ml medium to incubate cells for 3h at 0.5 moi ($1 \times 10^5$ 5′-UTR copies versus $2 \times 10^5$ hADSC cells). After gentle wash, HCVser-infected hADSC were cultured in 5 ml of fresh medium, with or without medium replacement every 7 days (pathway a or b, respectively).

Figure 11:
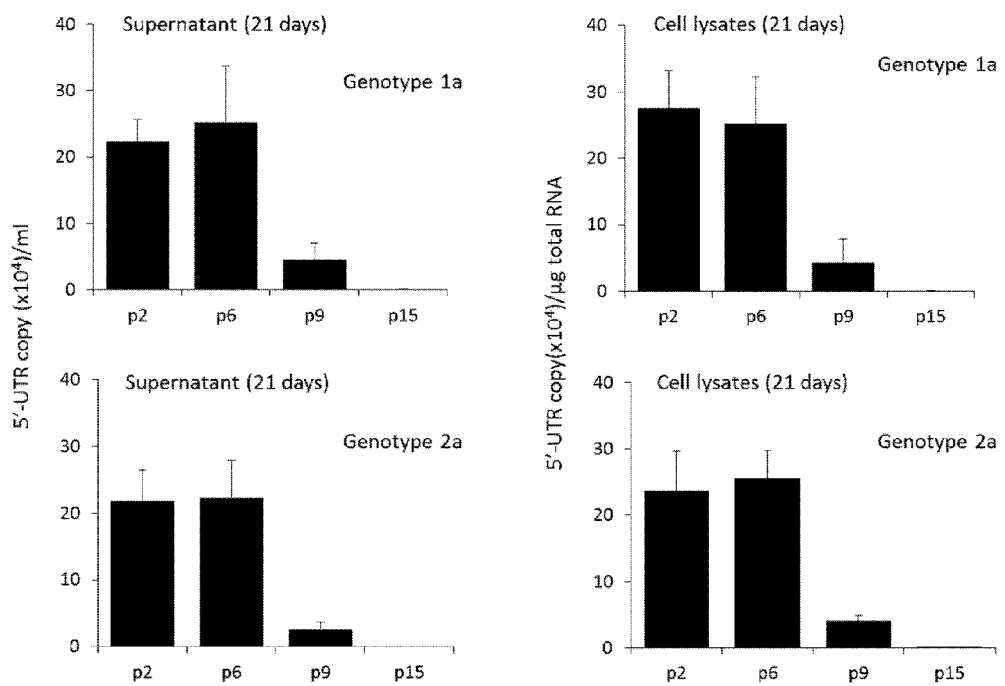

FIG. 11. Viral replication efficiency of p2 and p6 hADSC was superior to that of p9 and p15 cells. hADSC at different passages were exposed in suspension to HCVser-1a or -2a. After infection, viral 5′-UTR transcripts of 21 days' supernatants and cell lysates (continuous culture) were determined by qRT-PCR. Results showed that cells of p9 and p15 had significantly fewer viral copies in cell lysates and supernatants, in contrast to p2 and p6 cells. Data are expressed as mean±SD of 3 experiments.

Figure 3:
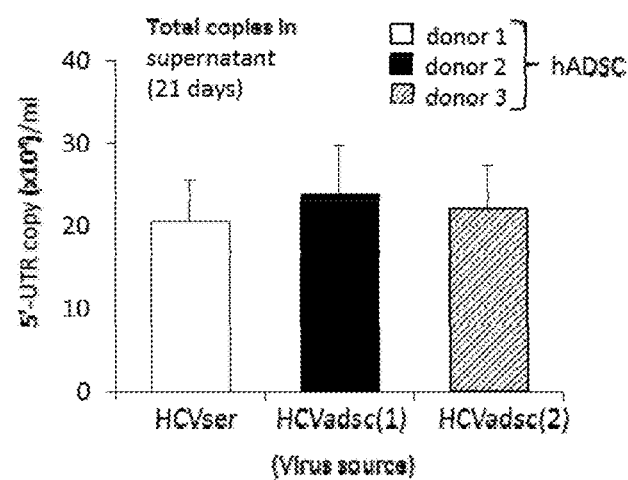
FIG. 3. HCVser infection is donor-nonspecific for cells and cross-genotypic for viruses and is mediated by various host factors except miR-122. (A) P-2 hADSC of "donor 1" were infected by HCVser-1b and the 21 days' supernatants (labeled as "HCVadsc(1)") were filtered through a 0.22-µm pore filter and used to infect p-3 hADSC of "donor 2", whose 21 day's supernatants (labeled as "HCVadsc(2)") were used to infect p-6 hADSC of "donor 3". Viral copy numbers in 21 days' supernatants were quantified by qRT-PCR. Data are expressed as mean±SD from triplicates of each batch of infected hADSC. (B) hADSC at p2, p6, p9 and p15 were infected by HCVser-1b, and viral transcripts in 21 days' supernatants (left) and cell lysates (right) were determined by qRT-PCR. Data are expressed as mean±SD from 3 independent experiments. (C) RT-PCR for DLK-1 expression of p0, p2, p6, p9 and p15 hADSC. All batches of cells were from the same donor. N: no reverse transcriptase as a negative control. Data are representative of experiments using cells from 3 different donors. (D) hADSC at p5 were infected by HCVser of mixed genotype 2a+2b and continuously cultured. On d21 and d56, cells were collected for RT-PCR to detect mRNAs encoding genotype-specific core antigens (174 bp for genotype 2a, left, and 123 bp for genotype 2b, right). N: d21 cells pulsed by HCV(−) control serum, as a negative control. P: HCV(+) serum per se as a positive control (mixed genotype 2a+2b). M: markers. Data are representative of experiments using sera from two HCVser genotype 2a+2b infected donors. (E) Flow cytometry for surface expression of CD81, LDL-R, SR-B1 and EGFR of p0, p2, and p6 hADSC. Black line: isotype control Ab. Red line: anti-CD81, -LDL-R, -SR-B1 or -EGFR Ab. Data are representative of 3 experiments for each passage of cells. (F) RT-PCR for the expression of occludin (OCLN), claudin-1 (CLDN1), NPC1L1, and miR-122 of p0, p2 and p6 hADSC (left panel). Data are representative of hADSC from 3 donors. N: no reverse transcriptase as a negative control. P: primary human hepatocytes isolated from HCV (−) individuals, as a positive control. The miR-122 expression was also determined by qRT-PCR in p0, p2, p6 hADSC, compared to Huh7.5 or HCV(−) primary human hepatocytes (PHH, right panel). Data are expressed as expression levels relative to p0 hADSC in mean±SD using hADSC and PHH from 3 different donors, respectively. (G) p2 hADSC were pretreated with indicated concentrations of blocking monoclonal anti-CD81 (clone JS-81), anti-LDL-R (clone C7), anti-EGFR Ab (clone LA1), or polyclonal anti-SR-B1 Ab for 1 h before pulse by HCVser-1b. For blocking Apo-E, indicated concentrations of anti-ApoE antibody (clone E6D10) were added into the HCVser, which was subsequently used for 3-hr incubation with hADSC. Viral 5'-UTR transcripts of the 21 days' supernatants were quantified. Isotype: treatment with isotype control antibody (100 µg/ml). Data are expressed as mean±SD of fraction inhibition (vs treatment with isotype Ab) from 3 experiments. Cell viability after each treatment was also evaluated by trypan blue. (11) p2 hADSC were transfected with siRNA specific for OCLN, CLDN1, NPC1L1, or DGAT-1. Transfection with scrambled RNA was used as a control. Forty-eight hours post-transfection, cells were washed and infected by HCVser-1b, and viral 5'-UTR copies in 21 days' supernatants were quantified. Knock-down of OCLN and CLDN1 was performed in the same experiment whereas knock-down of NPC1L1, or DGAT-1, was conducted in separate experiments. Cell viability was determined by trypan blue exclusion assay after each transfection and was not significantly changed in comparison to transfection by scrambled siRNA. Data are expressed as mean±SD of 3 independent experiments. (I) Adherent p4-p5 hADSC were infected by HCVser-1b and graded doses of ribavirin, telaprevir, and cyclosporine A were added in culture for continuous 21 days. hADSC were also incubated with graded concentrations of IFNα for 16 h before exposure to HCVser-1b. Cell viability was evaluated by trypan blue after each treatment. Data are expressed as mean±SD from 3 independent experiments.
Figure 3:
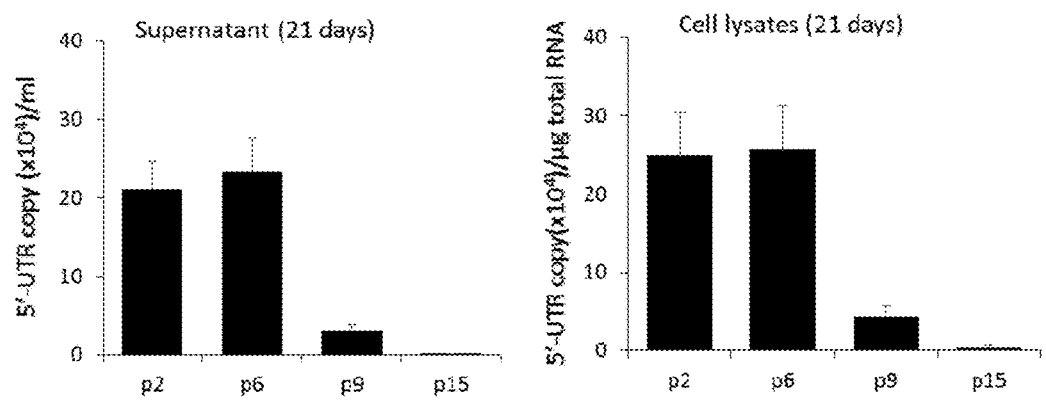
Figure 3:
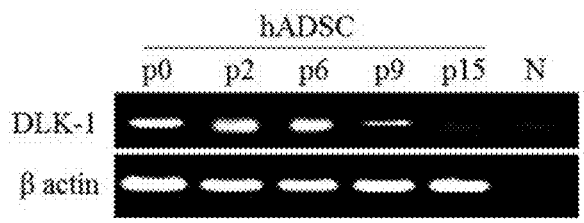
Figure 3:
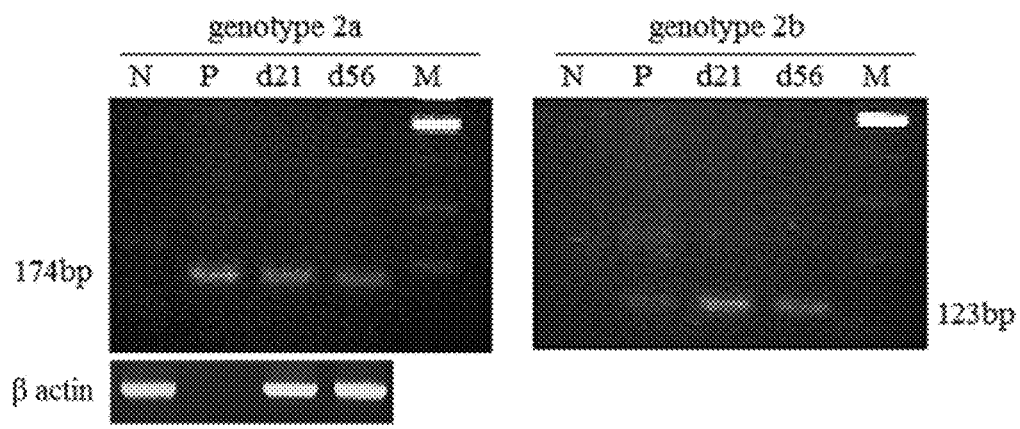
Figure 3:
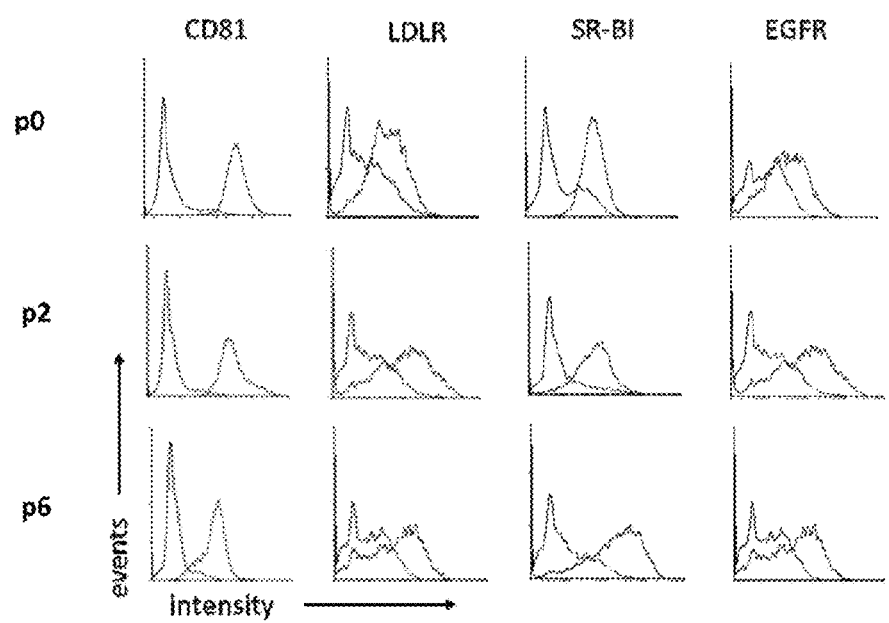
Figure 3:
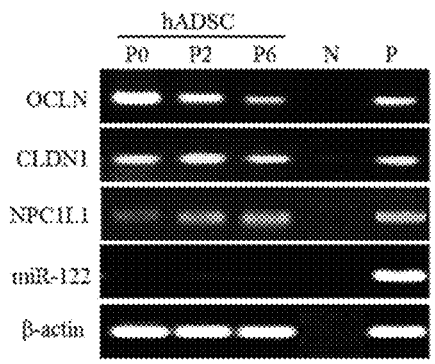
Figure 3:
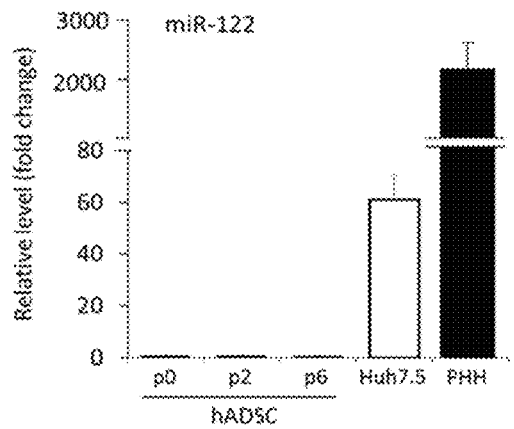
Figure 3:
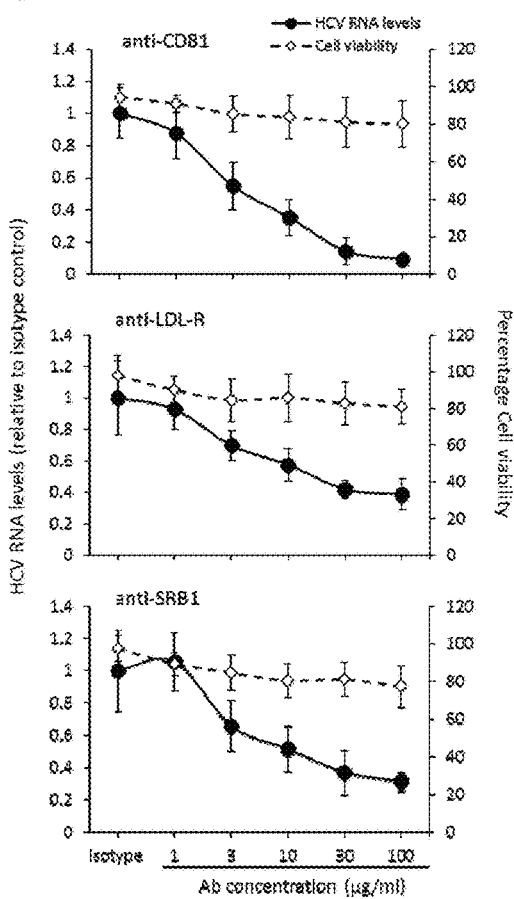
Figure 3:
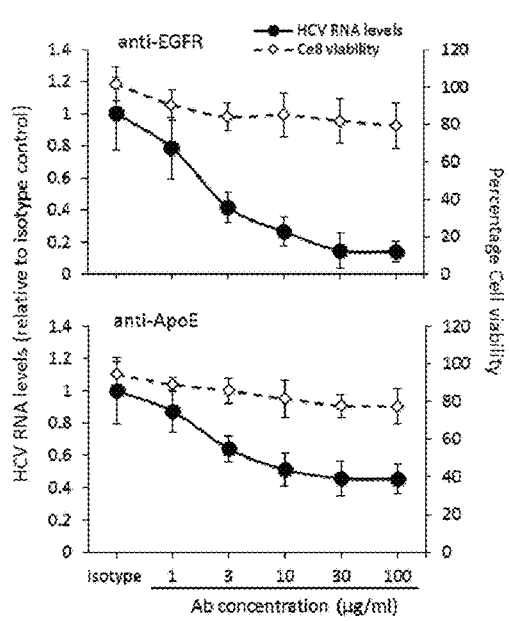
Figure 3:
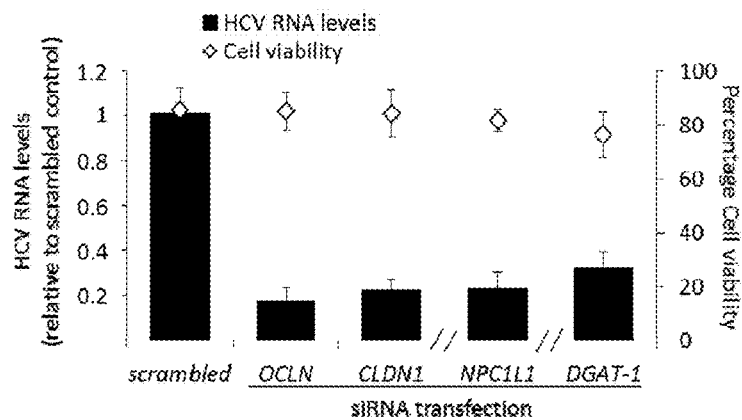
Figure 3:
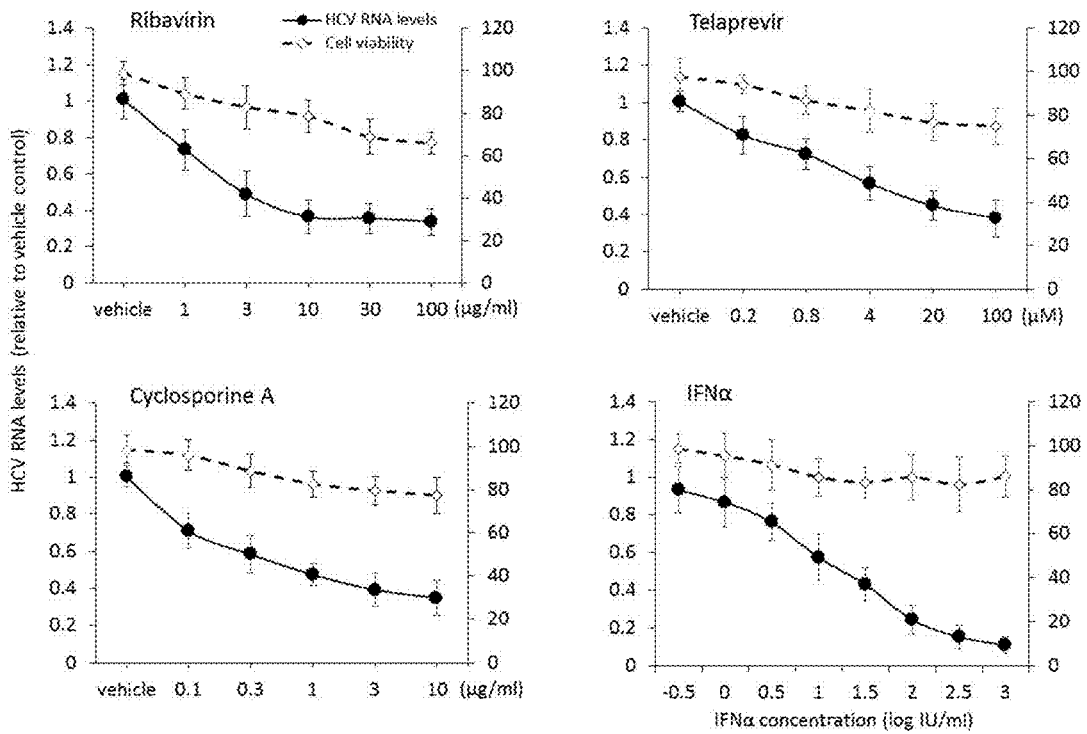
Figure 12:
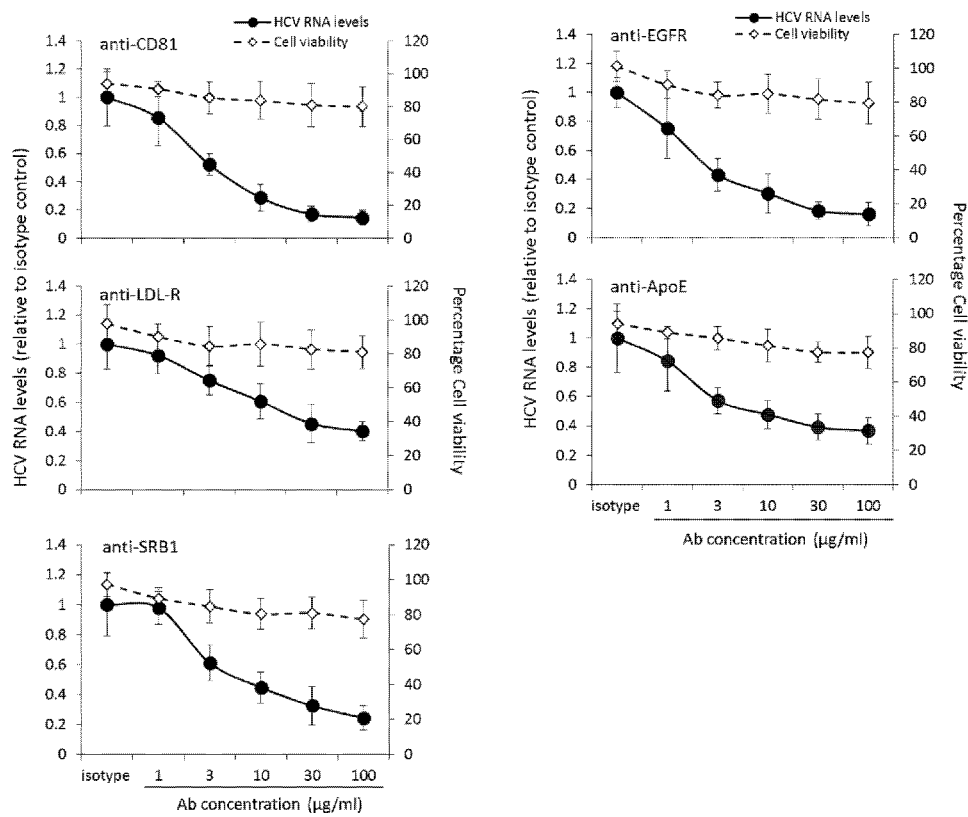

FIG. 12. Blockade of CD81, LDLR, SR-B1 and EGFR, and neutralization of ApoE, reduced viral copies in the cell lystaes of 21 days' HCVser-infected hADSC culture. P-2 hADSC was pretreatd with graded doses of monoclonal Ab against CD81 (clone JS-81), LDL-R (clone C7), EGFR (clone LA1), or polyclonal Ab against SR-B1 for 1 h, then washed before pulse with HCVser-1b. For ApoE blockade, various concentrations of anti-ApoE antibody (clone E6D10) were added into the HCV(+) serum, as described[14], for 1 h at room temperature, before use for 3-h incubation with hADSC. Consistent with the measurement in supernatants (FIG. 3G), blockade of CD81, LDL-R, SR-B1, EGFR of hADSC and neutralization of ApoE in the HCV(+) serum significantly reduced the amount of viral transcripts in cell lysates, in a dose-dependent manner. Meanwhile, treatment of antibodies per se did not significantly affect the hADSC viability. Data are expressed as mean±SD from triplicates for each treatment.

Figure 13:
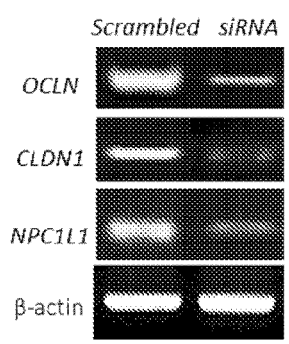
Figure 13:
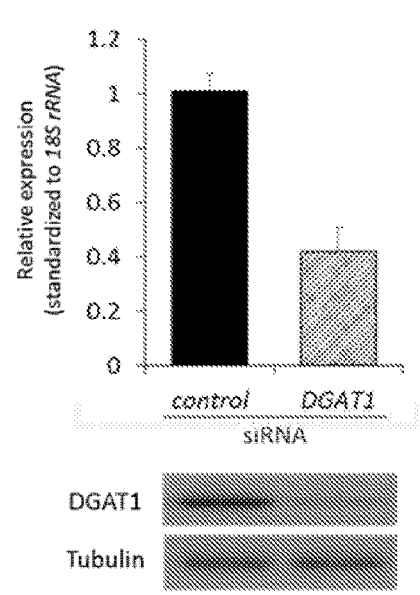
Figure 13:
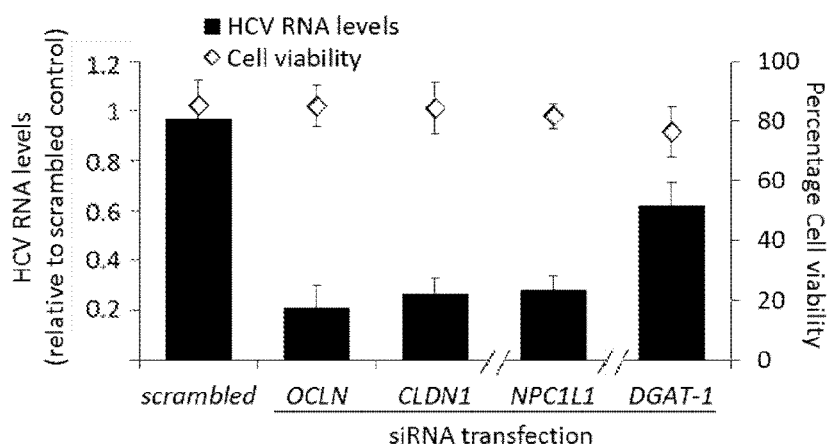

FIG. 13. RT-PCR after siRNA transfection and viral copy number in 21 days' cell lysates after knock-down of occludin (OCLN), claudin-1 (CLDN1), NPC1L1 or DGAT-1. (A) Knock-down of occludin, claudin-1 or NPC1L1 was performed as described[15,16] and RT-PCR was conducted as described[16-17]. Knock-down of OCLN and CLDN1 was performed in the same experiments, while knock-down of NPC1L1 was performed in separate experiments. Data are representative of 3 experiments. (B) siRNA probe for DGAT1 was predesigned siRNA from Ambion (catalog no. 11782 and 11784). Transfection of scrambled RNA and siRNA specific for DGAT1, qRT-PCR and western blot analysis were performed as described[18]. Data are expressed as mean±SD from 4 experiments and presented as relative ratios standardized to 18S rRNA. (C) After knock-down, hADSC were exposed to HCVser-1b and 5′-UTR copy numbers of 21 days' cell lysates were determined by qRT-PCR. The siRNA transfection per se did not significantly affect cell viability, compared to transfection with scrambled siRNA and determined by trypan blue exclusion tests 48 h after transfection. Apparently, DGAT1 knock-down had a more prominent inhibitory effect in supernatants than in cells (panel C vs FIG. 3H). This is consistent with findings that DGAT1 knock-down impairs both intracellular replication and release, but viral release appeared more markedly affected[19]. Data are expressed as mean±SD from 4 experiments and presented as relative ratio to transfection by scrambled controls.

Figure 14:
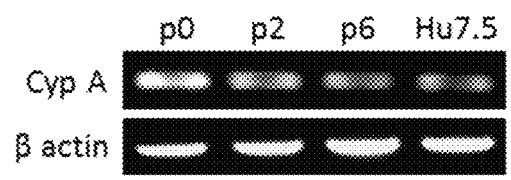

FIG. 14. RT-PCR for cyclophillin A expression in hADSC. RT-PCR for cyclophillin A (Cyp A) was performed in p0-p6 hADSC, as described[20]. Naive Huh7.5 cells were used as a positive control. Data are representative of 4 experiments.

Figure 15:
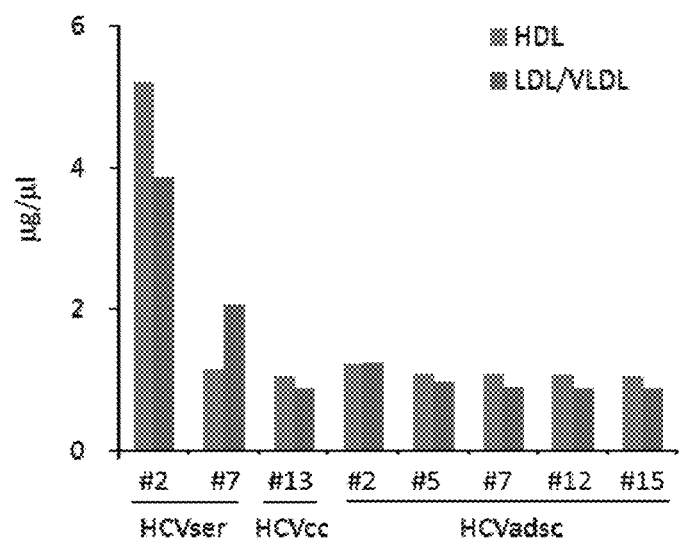
Figure 15:
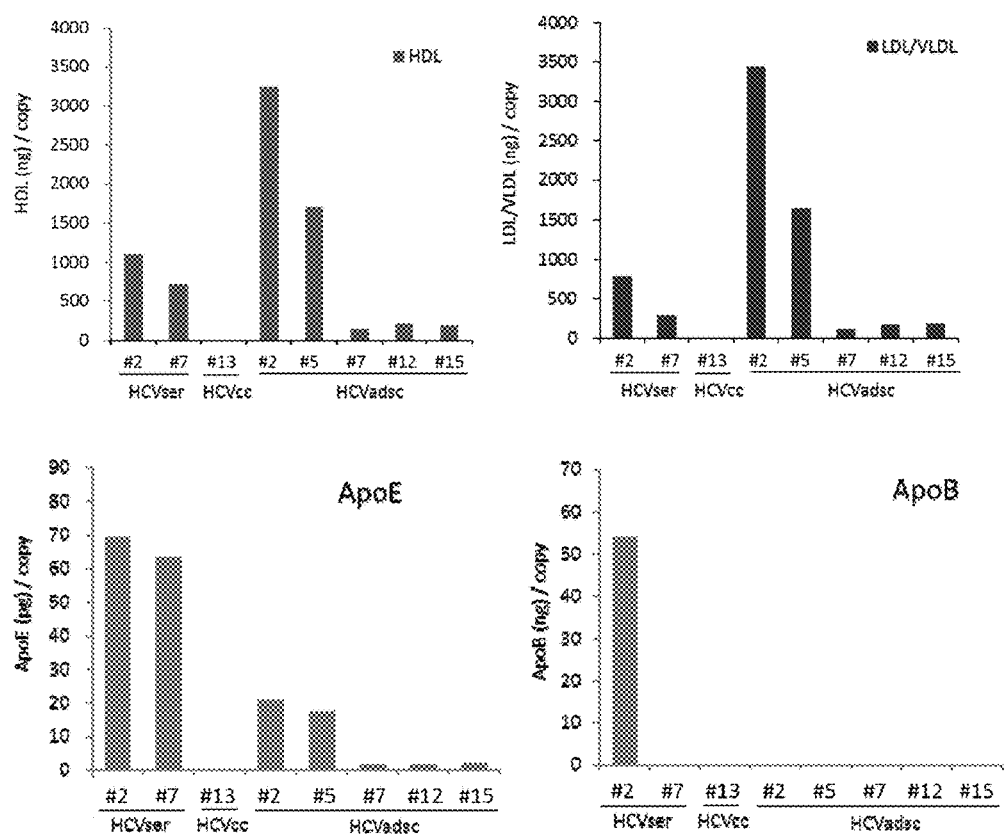
Figure 15:
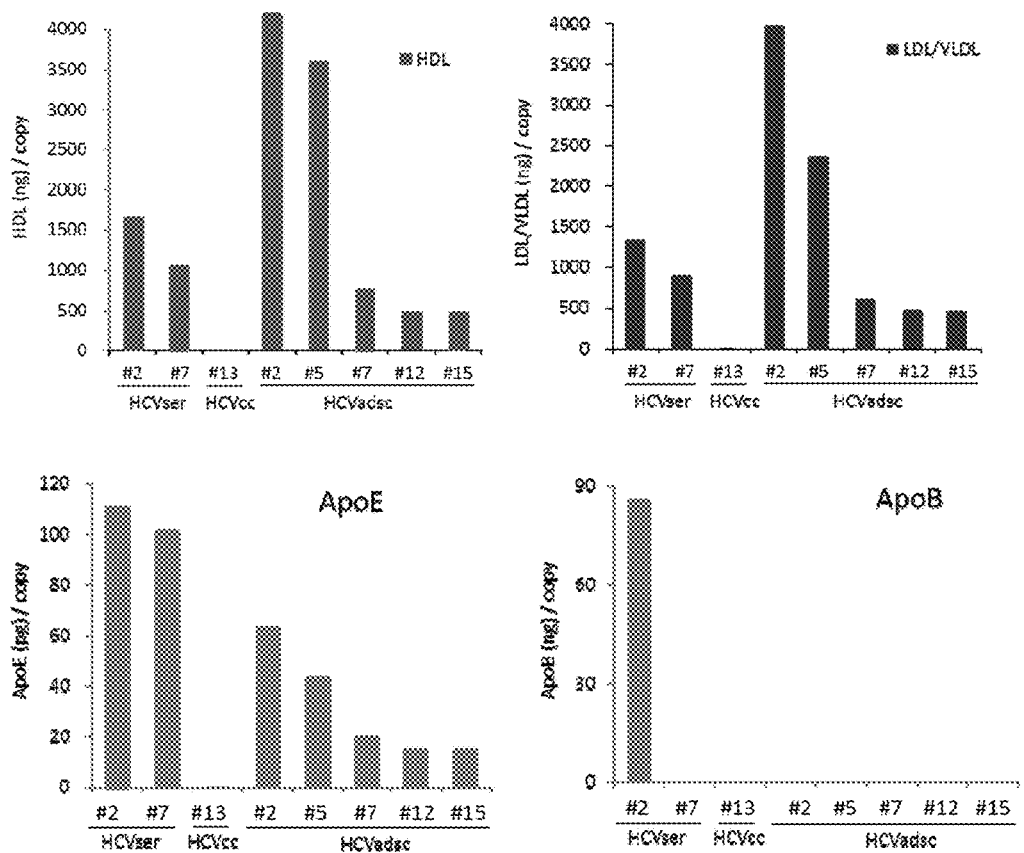

FIG. 15. Total lipid contents of the major fractions (by density gradient) of HCVser, JFH1/HCVcc and HCVadsc. Levels of HDL and LDL/VLDL were detected by the HDL and LDL/VLDL Cholesterol Assay Kit (Abcam). The amount of ApoB and ApoE were measured by the Quantikine® ELISA Human ApoB Immunoassay kit, and Quantikine® ELISA Human ApoE Immunoassay kit (R&D), according the manufacturer's instructions. The amounts of HDL and LDL/VLDL, ApoB and ApoE at different fractions were also normalized to weight per copy. (A) HCVser (particularly the fraction 2) had a higher "total" amount of HDL and LDL/VLDL than HCVcc or HCVadsc. (B) and (C) Analyses of another 2 batches of HCVser and HCVadsc showed the same patterns of lipid and ApoE/B contents.

Figure 4:
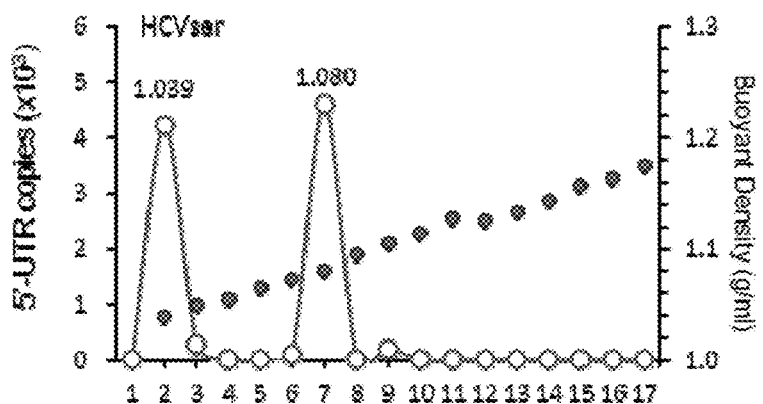
FIG. 4. HCVadsc differs from JFH1/HCVcc in physical properties and is infectious to primary human hepatocytes. (A) HCVadsc (genotype 2a) was harvested from 21 days' HCVser-2a infected hADSC supernatants and subjected to density gradient assay by equilibrium centrifugation in 10 to 40% iodixanol. Density gradient assays of HCVser (genotype 2a) and JFH1/HCVcc were also performed in parallel for comparison. Data are representative of 5 experiments. (B) HCVcc fraction 13 had the lowest amount of HDL and LDL/VLDL, when expressed as weight (ng) per viral copy. Data are representative of HCVser from 3 donors and their corresponding HCVadsc. (C) Measurement of the ApoE and ApoB demonstrated that major fractions of HCVser had the highest ApoE contents, followed by HCVadsc, whereas HCVcc fraction 13 had barely detectable ApoE (left panel). In contrast, ApoB was detected only in HCVser fraction 2 (right panel). Data are one experiment using HCVser (genotype 2a) and its corresponding HCVadsc (i.e., HCVadsc was generated by HCVser-infected hADSC), and are representative from 3 HCVser donors. (D) P2 hADSC in 6-cm petri dishes were exposed to HCVser (genotype 2a) or HCVcc. Infected hADSC were cultured for 14 or 21 days continuously (without medium replacement), and 5'-UTR copy numbers were quantified by qRT-PCR in the supernatants (left panel) and cell lysates (right panel) at the end of culture. Results showed that HCVcc did not infect/replicate in hADSC efficiently. Data are expressed as mean±SD from 3 experiments. (E) RT-PCR for viral 5'-UTR in supernatants of HCVcc-infected or uninfected Huh7.5 culture, as well as in 21 days' supernatants of HCVcc- or HCVser-infected hADSC. Data are representative of 3 experiments. (F) PHH isolated from HCV(−) patients were left for 3 days to allow attachment and then exposed for 3 h to 21 days' supernatants collected from hADSC infected by HCVser-1b or HCVser-2b, or pulsed by control serum. Five days post-infection, cellular RNAs were extracted for RT-PCR of 5'-UTR. HCVser-1b per se was used as a positive control. Data are representative of 3 experiments. (G) $1\times10^4$/well PHH isolated from 3 HCV(−) donors (donor 1, 2 and 3) were plated in 6-well plates for 3 days to allow cell attachment, and on day 4 PHH were infected separately by one of the 3 different batches of HCVser-1b (collected from 3 separate donors). HCVser-1b were used to generate the corresponding HCVadsc, which was also used to infect PHH in parallel. HCVser and its corresponding HCVadsc were paired to infect the same batch of PHH. Five days post-infection, PHH supernatants were collected and 5'-UTR copies were quantified. Exposure of PHH to HCV(−) control serum (also from 3 different donors) were used as negative controls. Data are expressed as mean±SD from triplicates of each infection.
Figure 4:
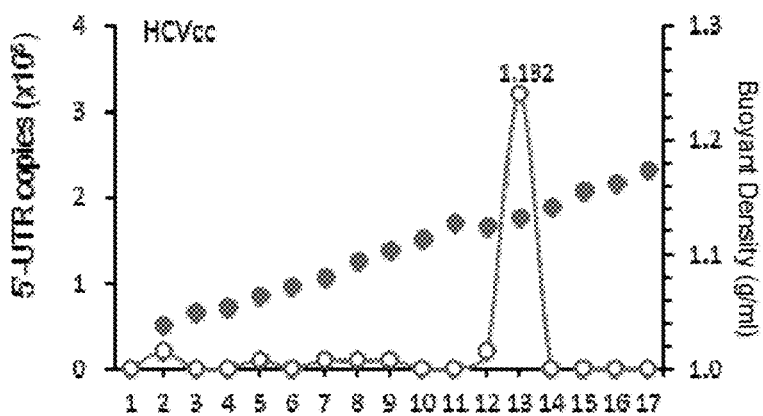
Figure 4:
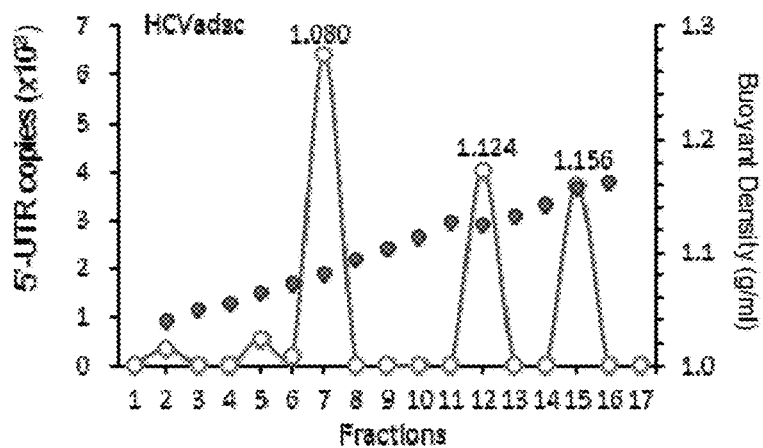
Figure 4:
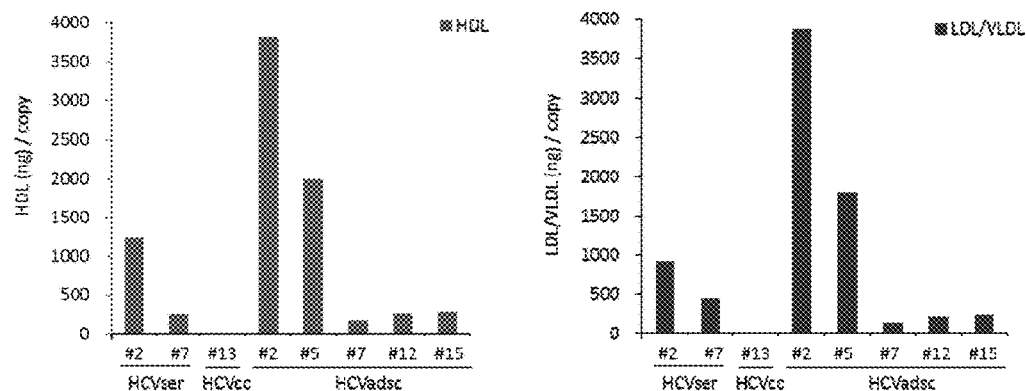
Figure 4:
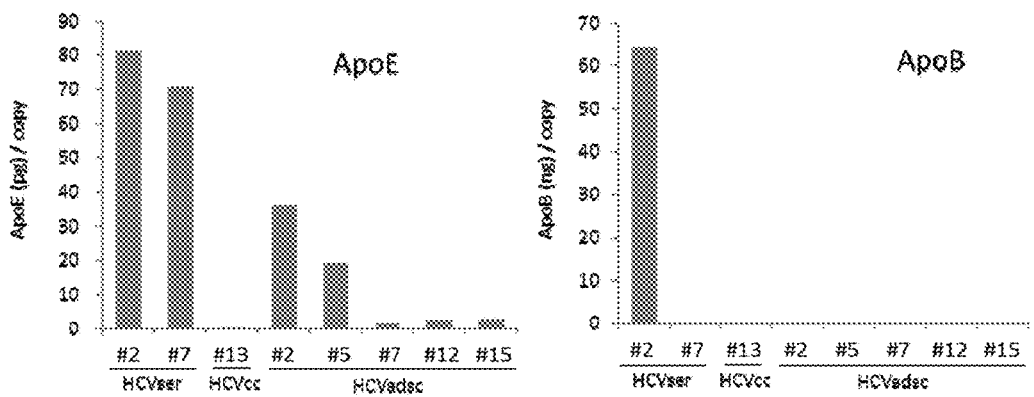
Figure 4:
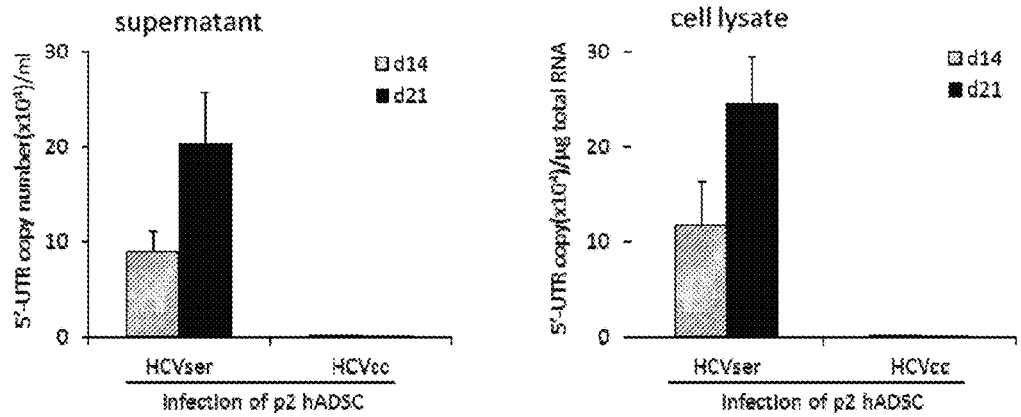
Figure 4:
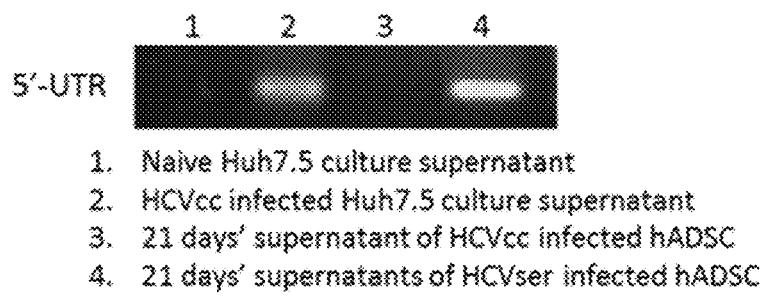
Figure 4:
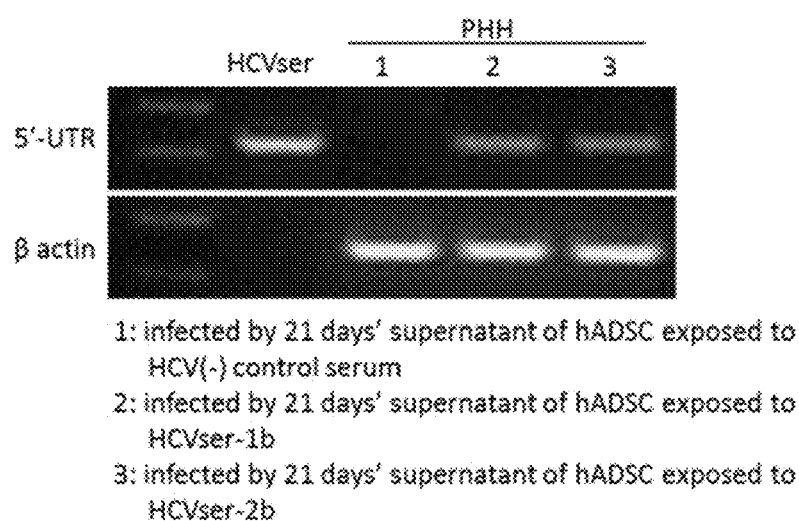
Figure 4:
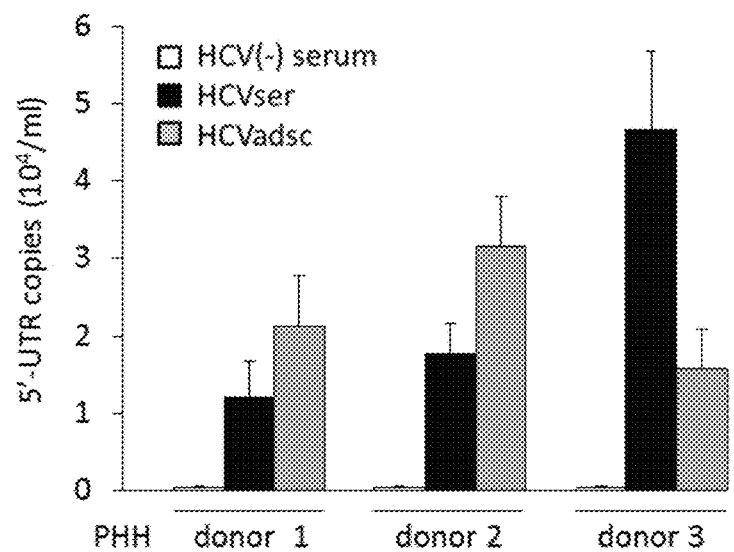
Figure 16:
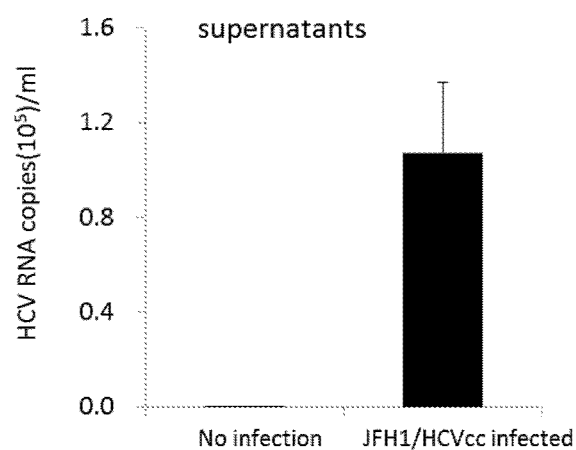

FIG. 16. JFH1/HCVcc infect Huh7.5 efficiently. $4 \times 10^5$ Huh7.5 cells/well were plated in 6-well plates overnight. After 1 day, cells were washed and incubated with HCVcc viral inoculum (0.5 moi) for 3 h. After washing, cells were cultured in DMEM supplemented with 10% fetal bovine serum (FBS) and 1% nonessential amino acids. On day 3 post-infection, supernatants were harvested and RNAs were extracted for qRT-PCR of 5′-UTR transcripts. Naive Huh7.5 cells without exposure to the viral inoculum were used as a negative control. Data are expressed as mean±SD from 3 experiments. This experiment validated the infectivity of HCVcc inoculum used for infection of hADSC (FIG. 4D).

DETAILED DESCRIPTION OF THE EMBODIMENTS OF THE INVENTION

Several aspects of the invention are described below with reference to exemplified applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

Definitions

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used here, the term "adipose tissue" defines a diffuse organ of primary metabolic importance made-up of white fat, yellow fat or brown fat. The adipose tissue has adipocytes and stroma. Adipose tissue is found throughout the body of an animal. For example, in mammals, adipose tissue is present in the omentum, bone marrow, subcutaneous space and surrounding most organs.

As used herein, the term "stem cell" defines an adult undifferentiated cell that can produce itself and a further differentiated progeny cell.

The terms "Human Adipose-Derived Stem Cell", "hADSC", "Human adipose-derived DLK-1⁺ stem cell", and "human adipogenic DLK-1⁺ cells" are used exchangeably, and as used herein is a human adult stem cell that is or has a parental cell that is obtained from a tissue source containing adipose tissue. These cells express a specific marker DLK-1 (i.e., Pref-1), a member of epidermal growth factor-like family[21] and critical for adipogenesis, and the expression is completely abolished in mature adipocytes[22-24].

The term "primary cells" as used herein refers to cells that are directly derived from cells or tissues from an individual. "Passaged cells" as used herein refers to cells subcultured from primary cells. "Passage number" as used herein refers to the number of times the cell has been subcultured from primary cells. For example, the passage 1 cells (P1 cells) refer to cells obtained by directly subculturing primary cells, and passage 2 cells (P2 cells) refer to cells obtained by directly subculturing the passage 1 cells, and so on.

As used herein, the terms "culture", "culturing", "grow", "propagate" and "propagating" are used exchangeably, and refer to the growing of cells in vitro in a prepared medium. As used herein, the terms "culture system", "culturing system", "propagate system", and "propagating system" are used exchangeably, and refer to a cell culture including cells generating viral particles. In particular, a culture system of the invention includes hADSCs in culture that generate HCV. The system supports complete replication (e.g., attachment, entry into cells, replication, maturation etc.) of HCV, including the production of infectious virus, in particular virus entry, replication comprising (−) and (+) strand synthesis, viral protein synthesis, virus assembly, virus trafficking, or virus release.

The term "sample" or "biological sample" as used herein means a biological material isolated from a subject or from in vitro culture. The biological sample may contain any biological material suitable for detecting a nucleic acid, polypeptide or other marker of a biologic, physiologic or pathologic process in a subject or in vitro cell culture, and may comprise culture media, body fluid, tissue, and cellular and/or non-cellular material obtained from a subject or in vitro cell culture.

As used herein, the term "diagnosis" refers to the determination of the presence of a disease or disorder. In some embodiments of the present invention, methods for making a diagnosis are provided which permit determination of the presence of a particular disease or disorder.

As used herein, the terms "patient," "subject," "individual," and the like are used interchangeably, and refer to any animal amenable to the methods described herein. In certain non-limiting embodiments, the patient, subject or individual is a human.

DESCRIPTION

The invention relates to the discovery that hADSCs are permissive for infection by HCV.

hADSC

Human adipose-derived stem cells are multi-potent adult stem cells of mesodermal origin and can be easily obtained in large quantities[9]. These cells express a specific marker DLK-1 (i.e., Pref-1), a member of epidermal growth factor-like family[21] and critical for adipogenesis, and the expression is completely abolished in mature adipocytes[22-24]. A growing body of evidence has demonstrated that human adipogenic DLK-1⁺ cells (hADSC) can differentiate into multiple cell lineages (for review, see reference[25-26]), making hADSC a promising tool for devising regenerative therapies. It has also been reported that mesenchymal stem cells at various anatomical compartments are susceptible to infection of viruses[27-32]. The role of hADSC in viral diseases, however, has not yet been explored.

In general, hADSCs can be obtained from any available sources. In one embodiment, hADSCs are separated from suitable tissue sources. Suitable tissue sources of hADSCs include, but are not limited to any fat-containing tissue, e.g., brown or white adipose tissue such as subcutaneous white adipose tissue. Typically, human adipose tissue is obtained from a living donor using surgical excision or liposuction. In some embodiments, the fat tissue is obtained from a pre-selected region on the subject, i.e., abdominal, hip, inguen, and peritoneum, or any combination thereof.

In one embodiment, hADSCs are isolated from abdominal or hip subcutaneous adipose tissue. In one embodiment, the hADSCs are primary cells, i.e. cells directly derived from adipose tissues of an individual. In another embodiment, the hADSCs are passaged cells, such as passage 1-15 cells, preferably passage 1-6 cells.

Methods to separate, isolate and expand ADSCs such as hADSCs are known in the art and described, for example in U.S. Pat. Nos. 6,391,2971B1; 6,777,231B1; U.S. Pat. No. 5,786,207; U.S. Patent Appl. Publ. No. 2005/0076396A1; Burris et al. (1999) Mol Endocrinol 13:410-7; Erickson et al. (2002) Biochem Biophys Res Commun. Jan. 18, 2002; 290(2):763-9; Gronthos et al. (2001) Journal of Cellular Physiology, 189:54-63; Halvorsen et al. (2001) Metabolism 50:407-413; Halvorsen et al. (2001) Tissue Eng. 7(6):729-41; Harp et al. (2001) Biochem Biophys Res Commun 281:907-912; Saladin et al. (1999) Cell Growth & Diff 10:43-48; Sen et al. (2001) Journal of Cellular Biochemistry 81:312-319; Zhou et al. (1999) Biotechnol. Techniques 13: 513-517; Erickson et al. (2002) Biochem Biophys Res Commun. Jan. 18, 2002; 290(2):763-9; Gronthos et al. (2001) Journal of Cellular Physiology, 189:54-63; Halvorsen et al. (2001) Metabolism 50:407-413; Halvorsen et al. (2001) Tissue Eng. Dec. 7, 2001; (6):729-41; Harp et al. (2001) Biochem Biophys Res Commun 281:907-912; Saladin et al. (1999) Cell Growth & Diff 10:43-48; Sen et al. (2001) Journal of Cellular Biochemistry 81:312-319; Zhou et al. (1999) Biotechnol. Techniques 13:513-517; Zulc et al. (2001) Tissue Eng. 7: 211-228; Hauner et al. (1987) J. Clin. Endocrinol. Metabol. 64: 832-835; Katz et al. (1999) Clin. Plast. Surg. 26: 587-603.

For the purpose of illustration only, several morphological, biochemical or molecular-based methods can be used to isolate the cells. In one aspect, hADSCs are isolated based on cell size and granularity since hADSCs are small and a granular. Alternatively, because stem cells tend to have longer telomeres than differentiated cells, hADSCs can be isolated by assaying the length of the telomere or by assaying for telomerase activity.

Alternatively, hADSCs can be separated from the other cells immunohistochemically by selecting for hADSC-specific cell markers. hADSCs express the mesenchymal stem cell markers CD10, CD13, CD29, CD34, CD44, CD54, CD71, CD90, CD105, CD106, CD117, and STRO-1. They are negative for the hematopoietic lineage markers CD45, CD14, CD16, CD56, CD61, CD62E, CD104, and CD106 and for the endothelial cell (EC) markers CD31, CD144, and von Willebrand factor (Zuk et al., *Mol Biol Cell* 13(12): 4279-4295, 2002; Musina et al., *Bull Exp Biol Med* 139(4): 504-509, 2005; Romanov et al., *Bull Exp Biol Med* 140(1): 138-143, 2005). Morphologically, they are fibroblast-like and preserve their shape after expansion in vitro (Zuk et al., *Mol Biol Cell* 13(12):4279-4295, 2002; Arrigoni et al., *Cell Tissue Res* 338(3):401-411, 2009; Zannettino et al., *J Cell Physiol* 214(2):413-421, 2008). In various aspects, hADSCs are isolated by immune-selection of DLK-1$^+$.

In another embodiment, hADSCs are obtained from commercially available sources, or established lines of hADSCs. Non-limiting examples of such hADSCs are such as Poietics™ Human Adipose-Derived Stem Cells (catlog # PT-5006, Lonza Group Ltd.), and ATCC® PCS-500-011™.

Cell Culture

In general, hADSCs can be maintained and expanded in culture medium that is available to and well-known in the art. Such media include, but are not limited to, Keratinocyte-SFM (K-medium), Dulbecco's Modified Eagle's Medium® (DMEM), DMEM F12 Medium®, Eagle's Minimum Essential Medium®, F-12K Medium®, Iscove's Modified Dulbecco's Medium® RPMI-1640 Medium®, Mesenchymal Stem Cell Basal Medium (ATCC® PCS-500-030™) and Mesenchymal Stem Cell Growth Kit-Low Serum (ATCC® PCS-500-040™).

Also contemplated in the present invention is supplementation of cell culture medium with mammalian sera, preferably fetal calf serum. In some embodiments of the present invention, such mammalian sera concentrations range between 0 vol % and 20 vol %, preferably between 5 vol % and 15 vol %, more preferably 10 vol %. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, serum replacements and bovine embryonic fluid.

Additional supplements such as growth factors, hormones, amino acids, lipids, minerals, etc. also can be used advantageously to supply the cells with the necessary trace elements for optimal growth and expansion. Such supplements are commercially available. It is well within the skill of one in the art to determine the proper concentrations of these supplements.

HCV

HCV according to the invention can be any HCV that can infect hADSCs or any HCV that can be separated from HCV infected individuals. In one embodiment, HCV is at least one of the HCV genotypes selected from the group consisting of genotype 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, or any combination thereof. In another embodiment, HCV is at least one of the HCV genotypes selected from the group consisting of genotype 1a, 1b, 2a, 2b, and mixed 2a+2b.

In one aspect, the invention includes a hADSCs-based system for propagating HCV, which comprises hADSCs. In another aspect, the invention includes a method of using hADSCs or the HCV culture system of the present invention for propagating HCV, or conducting HCV life cycle analyses, or diagnosing HCV infections, or screening of anti-viral compounds, or characterizing the HCV of a subject infected with HCV.

The level of HCV can be determined by any known technique in the art. Such techniques may include anti-HCV ELISA assay (Enzyme Linked ImmunoSorbent Assay), which tests for HCV proteins. Testing for HCV replication by amplification tested RNA (e.g. polymerase chain reaction or PCR, branched DNA assay) may be used. The synthesis of the RNAs of the HCV may be indeed analysed by RT-PCR in a single step using a device designed for real time PCR or by hybridization of the RNAs on filters using HCV-specific radioactive probes. For instance, the isolated RNA may be subjected to coupled reverse transcription and amplification, such as reverse transcription and amplification by polymerase chain reaction (RT-PCR), using specific oligonucleotide primers that enable amplification of HCV genome. Then a direct sequencing may be performed to determine the genotype of HCV that has infected said subject.

In various embodiments, the level of HCV is determined by measuring the HCV titre, the level of an HCV nucleic acid, or the level of an HCV polypeptide.

In various embodiments, a decrease in the level of HCV observed in the presence of a candidate compound, relative to the level HCV observed in the absence of the candidate compound, is indicative of the inhibitory activity of the candidate compound.

According to invention, candidate compounds include without limitation a chemical compound, a protein, a peptide, a peptidomemetic, an antibody, a nucleic acid, an antisense nucleic acid, an shRNA, a ribozyme, and a small molecule chemical compound.

As disclosed herein, the anti-HCV compounds identified using the screening methods can be further tested in susceptible animal models.

Kits

In a related aspect, the invention also provides a kit for propagating HCV, or conducting HCV life cycle analyses, or diagnosing HCV infections, or screening of anti-viral compounds, or characterizing the HCV of a subject infected with HCV, comprising hADSCs as described herein, and culture medium suitable for culturing hADSCs.

The invention is further illustrated by the following examples. These examples are only intended to illustrate the invention, but not to limit the scope of the invention. For the experimental methods in the following examples, they were performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLES

Materials and Methods

Clinical Samples

All clinical fatty tissues and liver samples were obtained from the Kaohsiung Medical University Hospital with approval from the institution research committee (KMUH-IRB-960477, KMUH-IRB-960343 and KMUH-IRB-20120404). Written informed consents were obtained from all donors prior to the procedures.

Fractionation of Fresh Fatty Tissues and Culture of DLK-1+ Cells

HCV(+) fatty tissues were obtained from the surgical wounds (laparotomy) for resecting the hepatocellular carcinomas. For HCV(−) fatty tissues, samples were obtained from the transverse rectus abdominis myocutaneous flaps of women who had received breast reconstruction immediately after mastectomy for breast cancer, as previously described[13]. HCV(−) fatty tissues were also obtained from obese persons receiving liposuction (Table 1). None of the patients had received adjuvant chemotherapy or radiation therapy for management of breast cancer before the surgery.

After sample harvesting, tissues were washed with sterile normal saline and specimens were put in a sterile bag and immediately sent for preparation. Fresh fatty tissues were either fixed for immunohistochemistry or used for fractionation by centrifugation (800 g, 10 min) into a floating layer (floater) at the top (which contained mature adipocytes and connective tissues), a buffer layer in the middle, and a sedimented cell pellet at the bottom, as described[12,13,33]. Briefly, fat tissues were thoroughly minced into small pieces with scissors, and washed with PBS without calcium and magnesium and subsequently digested with 0.075% collagenase (37.5 mg/mL; Sigma-Aldrich) by constant agitation at 37° C. in PBS for 30 min.

The cell pellet (i.e., SVF cells) in the bottom layer was collected and treated with RBC lysis solution (to lyse the erythrocytes) as described[12,34], and subsequently filtered through a 100-μm Steriflip (Millipore) filter. The number and viability of SVF cells were determined using a Countess Cell counter (Invitrogen) after staining with trypan blue. SVF cells were then subject to positive selection for DLK-1+ cells by immunomagnetic beads, as described[10], and cellular RNAs were extracted for RT-PCR or qRT-PCR. DLK-1+ cells were also subjected to immunocytochemistry (for viral NS5 antigen).

For all samples, the interval from fat sampling to isolation of cells was 3 h or less. For culturing DLK-1+ cells, 1×10$^5$ cells were placed in 6-cm petri dishes for 49 days, as described[13]), and supernatants were harvested every 7 days (synchronizing with medium replacement) for RNA extraction.

Immunoselection of DLK-1+ Cells

RBC-lysed unfractionated SVF cells; prepared from HCV-infected or -uninfected individuals, were incubated with polyclonal rabbit anti-DLK1 antibody (Abeam, USA) at 4° C. for 30 minutes. Cells were washed twice in HBSS containing 0.8 mmol/L, MgCl$_2$, 20 mmol/L HEPES, 100 U/mL penicillin, and 100 μg/mL streptomycin and incubated with goat anti-rabbit IgG bound to magnetic microbeads (Miltenyi Biotec Inc, Auburn, Calif.) at 4° C. for 30 minutes, as described[10]. Cell suspensions were washed and passed through a column in a MidiMACS Separator (Miltenyi Biotec), resulting in retaining of DLK-1+ cells in the column with pass-through of the DLK-1− cells. Both cell fractions were washed twice in HBSS. The cell viability was >96% and >97% for DLK-1+ and DLK-1− fractions, respectively. RNAs were extracted for RT-PCR or qRT-PCR. In separate experiments, cells were fixed to cytospin slides for immunocytochemistry (5-7×10$^3$ cells/slide). In experiments of in vitro infection, DLK-1+ cells were cultured and passaged (sub-cultured, as described[13]) for indicated time periods after exposure to HCV(±) serum (HCVser). RNAs were then extracted for RT-PCR or qRT-PCR, of viral 5'-UTR transcripts.

hADSC Infection with HCVser

Two protocols were adopted in this study:

(1) Protocol 1, Infection in Suspension—

We used passage-2 (p-2) to -6 of naive hADSC for HCVser infection. A total of 200 μl of HCV serum (containing 1×10$^5$ 5'-UTR copies) was added to 5×10$^5$ hADSC suspended in 800 μl of fresh culture medium at a multiplicity of infection (MOI) of 0.2 in Eppendorf tubes, and subsequently incubated at 37° C. for 3 hours. Cells were washed 3 times with PBS and further cultured for 7, 14, 21, and 28 days, and RNAs in supernatants and cell lysates were harvested for RT-PCR of 5'-UTR. Cells were also collected for immunocytochemistry and transmission electron microscopy (TEM) study.

(2) Protocol 2, Infection in Adherent Form—

P-2 to p-6 naive hADSC were plated in 6-cm petri dishes for 1 day to allow cell attachment, and HCVser was added in a final volume of 2-ml medium for 3 h at 0.5 moi (1×10$^5$ 5'-UTR copies versus 2×10$^5$ hADSC cells). After gentle wash, cells were cultured in 5 ml fresh medium with or without medium replacement every 7 days.

RT-PCR and Quantitative RT-PCR for 5'-UTR

RNAs were extracted from 140 μl HCV(+) serum or supernatants of HCVser-infected hADSC culture with QIAamp® Viral RNA Mini Kit (Qiagen, Basle, Switzerland). RNAs from cell lysates were isolated using PureLink® RNA Mini Kit (Ambion, Carlsbad, Calif., USA), according to the manufacturer's instructions. RNA was then converted into single-stranded cDNA with the high-capacity cDNA reverse transcription kit, followed by PCR with the GoTaq Master Mix (Promega, WI, USA). For quantifying viral copies, PCR was performed with the Hepatitis C Virus Advanced kit (PrimerDesign Ltd., UK) using Applied Biosystems® ViiA™ 7 Real-Time PCR System. HCV-specific reverse and amplification primers were designed according to ABI primer3.0 Express Soft Word. Primer 5'-ACTCG-CAAGCACCCTATCAG-3' was used for the reverse transcription and the primers used for PCR and real-time PCR were matched to the highly conserved 5'-untranslated region (UTR) of different HCV genotypes, as described[35].

Immunohistochemistry (IHC) on Human Fatty Tissues

Fresh fatty tissues were harvested from the surgical wounds, fixed in formalin and embedded in paraffin. Tissues were cut into 5 μm sections and de-waxed, then immersed in the citrate buffer (10 mM Citric Acid, pH 6.0) and heated by microwave for antigen retrieval. After blocking with 5% BSA at room temperature for 30 min, polyclonal rabbit anti-DLK1 antibody (1:150; Cat. No. ab21682, Abcam, USA) or rabbit IgG Ab (1:150, Cat. No. AB-105-C, R&D) was applied at 4° C. overnight, followed by alkaline phosphatase-conjugated anti-rabbit IgG secondary antibody (1:500; Jason ImmunoResearch) for 1 h at room temperature and the color was subsequently developed with a fast red substrate system (Sigma-Aldrich). For sequential NS5 staining, samples were immersed in the PBS for 10 min to remove the coverslips, and slides were incubated in 0.3% $H_2O_2$ for 30 min at room temperature to reduce non-specific background from endogenous peroxidase. After blocking with 5% BSA for 30 min at room temperature, mouse anti-NS5 antibody (1:200, clone BGN/1246/5G7, Cat. No. 0200-0423, AbD Serotec) or mouse IgG1 isotype Ab (1:100, Cat. No. 14-4714, eBioscience) was added at 4° C. overnight. In our experiences, cell permeation procedure was not required for NS5 staining on fatty tissues, as samples had been embedded in paraffin before. Sections were then incubated with horseradish peroxidase polymer Quanto reagent (anti-mouse, ready to use; Thermo Scientific) for 7 min at room temperature and color was developed with UltraVision Quanto Detection System (containing DAB substrates for color development; Thermo Scientific). Afterwards, sections were stained with hematoxylin and the coverslips were re-placed back, which caused slight change of the cell contour (as presented in FIG. 1E). The electronic images of DLK1 and NSSA staining were captured by a high quality microscope (Zeiss), fast computer hardware and high-resolution screens with TissueFAXS scanning software (TissueGnostics). The same fields in the images were subsequently selected and visualized for comparison and analysis for colocalization. In fatty tissues (FIG. 1E), the optimal time required for color development varied remarkably among tissues from different donors (i.e., donor-to-donor variations), regardless of HCV infection status. We have modified the methods many times and discovered that the time for color development is critical. The principle we followed was, first, to determine the maximal time for color development which yielded least color signals for isotype Ab staining (rabbit IgG or mouse IgG1), and then adopted this time period for color development of anti-DLK-1 Ab or anti-NS5 Ab staining. This was to ensure that little false positivity be caused by over-development of the substrates and a low background for isotype Ab staining be obtained.

In our study on fatty tissues of HCV(+) donor 1 (Table 1), the maximal time for color development of rabbit IgG staining was 40-50 seconds before significant color signals appeared, so color development for DLK-1 staining was set for 40-50 sec. Similarly, the maximal time for color development of mouse IgG1 staining without significant color signals was as short as 15 seconds, which was set to be the color development time for anti-NS5 Ab staining. In contrast, on fatty tissues of donor 2 and donor 3, the optimal color development time for rabbit IgG staining was 30 seconds and that for mouse IgG1 staining was only 10 seconds, so these time periods were set for the color development of anti-DLK-1 and anti-NS5 Ab staining, respectively. Similar principles were followed when staining HCV (−) samples.

Immunocytochemistry (ICC)

Figure 2:
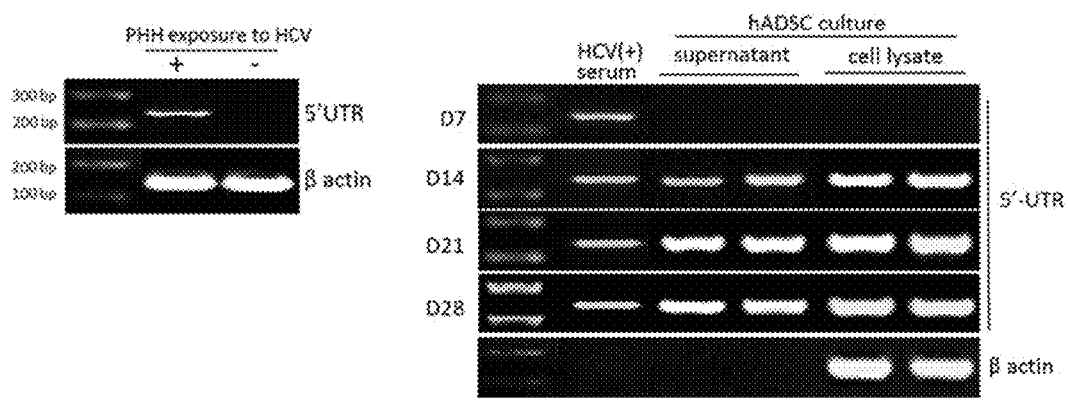
FIG. 2. Naive DLK-1$^+$ hADSC are permissive of serum-borne HCV infection in vitro. (A) Primary human hepatocytes (PHH) were isolated from HCV(−) donors and placed in dishes for 3 days before pulse with HCVser (lane "+", left panel) or HCV(−) control serum (lane "−", left). After 3 h pulse, PHH were cultured for additional 5 days and RNAs were extracted for RT-PCR of 5'-UTR (left panel). In parallel, p-3 or p-4 DLK-1$^+$ hADSC isolated from HCV(−) donors were pulsed in suspension by HCVser at 0.2 moi with medium replacement every 7 days. At indicated time points, the supernatants and cells were harvested separately and RNAs were extracted for RT-PCR of 5'-UTR. Data are representative of 10 experiments. RNAs of HCV(+) serum was also extracted for RT-PCR as a control. (B) Supernatants and cells of d14 and d28 HCVser-1b infected hADSC were collected and RNAs were extracted for RT-PCR of HCV-specific negative strand RNA. Data are representative of 4 experiments. *: day-0 culture supernatants harvested 1 h after washing post-infection with HCVser. (C) d14 hADSC pulsed by HCVser-1b or HCV(−) control serum were spun onto cytospin slides for triple staining with rabbit anti-human DLK-1 antibody (red label, panels b & f), followed by mouse anti-NS5 antibody (panels d & h; brown label in d) and hematoxylin (blue label, c, d, g and h) on the same sections. DLK-1$^+$ hADSC infected by HCVser contained NS5A (panel b vs d), whereas cells pulsed by HCV(−) control serum expressed DLK-1 without NS5 (panels f vs h). Staining with rabbit IgG and mouse IgG1 was used as negative controls (panels a & e, and c & g, respectively). Results are representative of 4 experiments. (D) Transmission electron micrographs of d14 (panels b & c) and d21 (panels e & j) HCVser-1b infected hADSC. D14 and D21 cells exposed to HCV(−) control serum were shown in panels a & d. Inlets of panels b-f are magnification of the yellow squares or yellow arrows. White arrows in the inlets of panels b, c, e & f indicate viral particles, and the white arrow in the inlet of panel d indicates an onion-shape membrane structure of the uninfected hADSC. Data are representative 2 experiments from infection by HCVser-1b and 1 experiment from infection by HCVser-2a. (E) qRT-PCR of viral 5'-UTR in cell lysates (left panel) and supernatants (right panel) of HCVser-1b infected hADSC collected every 7 days. Data are expressed as mean±SD from 3 experiments. (F) Viral 5'-UTR copies (by qRT-PCR) were quantified in supernatants of HCVser-1b infected hADSC continuously cultured for 1 to 4 weeks. Data are expressed as mean±SD from 4 experiments.
Figure 2:
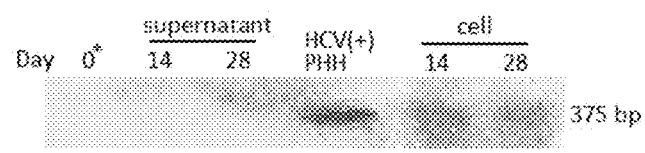
Figure 2:
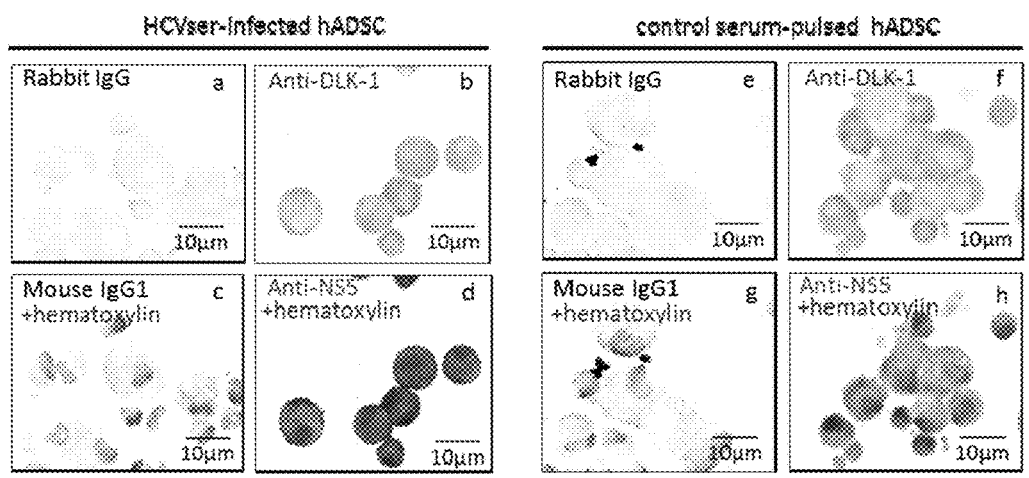
Figure 2:
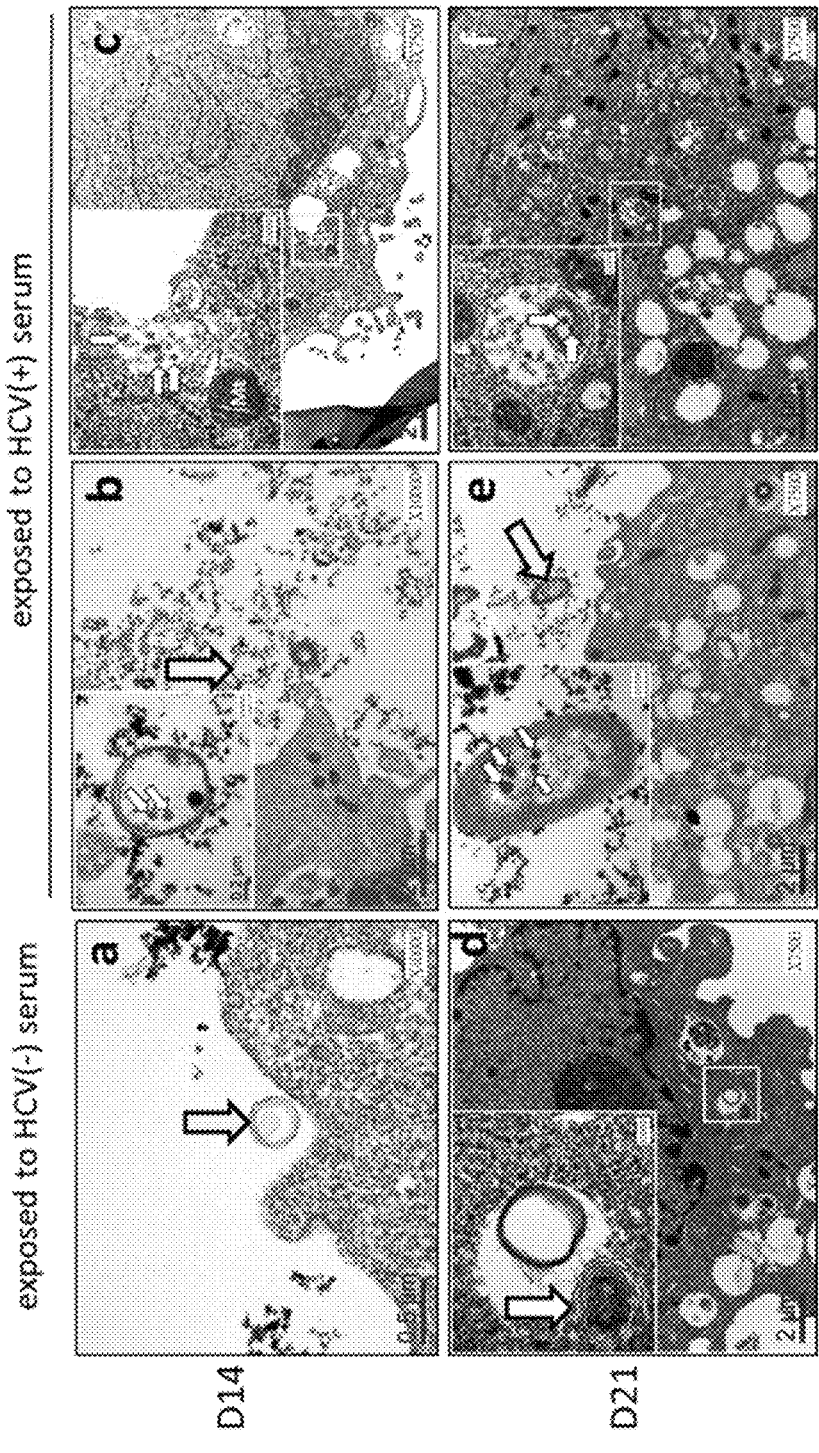
Figure 2:
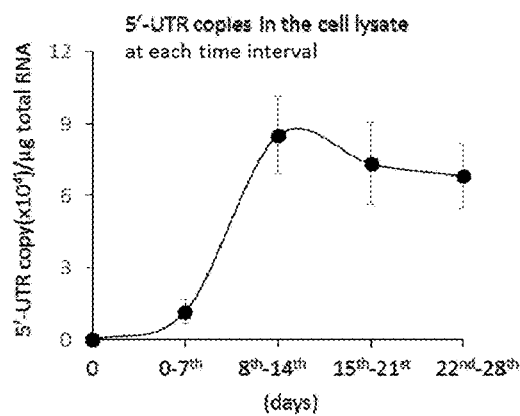
Figure 2:
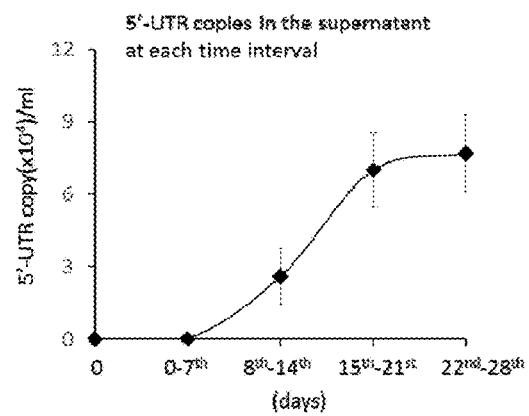
Figure 2:
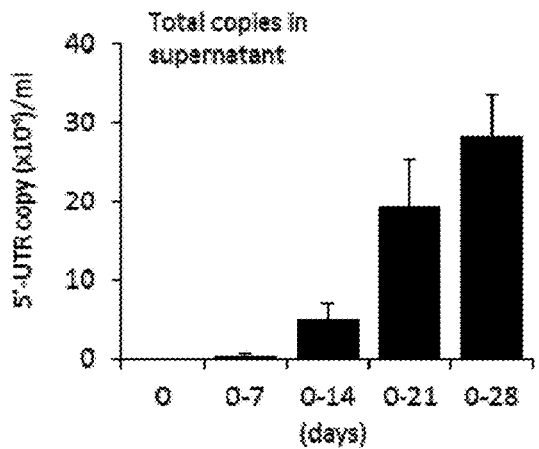

For immunocytochemistry of unfractionated SVF cells or DLK-1[+] hADSC, or DLK-1[−] cells, similar principles were followed as for IHC, and the optimal time for color development was pre-determined in every control experiment, as described above. Cells were collected at indicated time points and adhered to polylysine-coated glass slides by cytospin, and subsequently fixed with 4% formalin for 20 minutes. For DLK-1 staining, cells were subjected to antigenic retrieval by 0.05% trypsin solution for 30 min at 37° C. and then rinsed by DDW for 3 times. After blocking with Ultra V Block buffer (reagent in the UltraVision Quanto Detection System, Thermo, USA) for 5 min, cells were incubated with rabbit anti-DLK1 antibody or rabbit IgG at 4° C. overnight, followed by alkaline phosphatase-conjugated anti-rabbit IgG secondary antibody for 1 h at room temperature and developed for 5-6 min (in most cases) with a fast red substrate system (Sigma-Aldrich). For single or sequential staining of HCV-specific NS5 (which was stained on the same slides, as shown in FIG. 2C), slides were placed in the PBS for 10 min to remove the coverslips and to wash out the mounting media, and cells were permeated and blocked for 30 min with PBS containing 0.3% Tritox-100 and 1% BSA, prior to the application of UltraVision Quanto Detection System (Thermo Scientific, Fremont, Calif., USA). Cells were then incubated in Hydrogen Peroxide Block (Abcam, MA, USA) for 10 minutes to reduce the nonspecific background staining due to the endogenous peroxidase. After washing, cells were incubated with Ultra V Block (Thermo Scientific, MA, USA) for 5 minutes to block the nonspecific background staining, and incubated overnight at 4° C. with dilution buffer containing mouse monoclonal anti-NS5 antibody. Staining with mouse IgG1 was used as a negative control. The following day, cells were incubated with Primary Antibody Amplifier Quanto solution for 10 minutes and HRP Polymer Quanto for another 10 minutes, and washed by PBS between each reagent application. Finally, 30 μl DAB Quanto Chromogen was added to 1 ml DAB Quanto Substrate, mixed by swirling and applied to cells for 2-3 minutes (in most cases) for color development. After washing, slides were mounted with permanent mounting medium, covered by coverslips, and visualized using TissueFAXS microscopy (ZEISS) and photographed.

Transmission Electron Microscopy for Serum HCV-Infected hADSC

For TEM study, hADSC were collected and prepared as described[36], and was examined by a transmission electron microscope (JEM2000 EXII; JEOL, Tokyo, Japan).

RT-PCR for mRNA Encoding Core Antigens of HCV 2a and 2b

RNAs of hADSC were isolated using the PureLink® RNA Mini Kit (Ambion, Carlsbad, Calif., USA) following manufacturer's instructions. RNAs were converted into single-stranded cDNA with the high-capacity cDNA reverse transcription kit (Applied Biosystems). The specific primer used for the reverse transcription was 5'-ATGTACCCCAT-GAGGTCGGC-3'. Primers used for PCR were matched to the core protein region of different HCV genotypes. The primer mixture containing (forward) 5'-CGCGCGACTAG-GAAGACTTC-3' and (reverse) 5'-CGCGCGACGCG-TAAAACTTC-3' was used for the 1st PCR, with a thermal profile at the following settings: 94° C. for 2 min followed by 35 cycles of 94° C. for 45 sec, 55° C. for 45 sec and 72° C. for 90 sec, and then 72° C. for 7 mins for final extension. Type-specific antisense primers used for genotype identification in the 2nd PCR were 5'-CCAAGAGGGACGGGAACCTC-3' (type 2a) and 5'-ACCCTCGTTTCCGTACAGAG-3' (type 2b) with a thermal profile at the following settings: 95° C. for 2 min followed by 30 cycles of 95° C. for 30 sec, 60° C. for 30 sec and 72° C. for 30 sec, and then 72° C. for 7 min for final extension[37,38].

Flow Cytometry and Blocking Experiments 0.5-1×10$^5$ hADSC at different passages in suspension were stained with mouse anti-human CD81 monoclonal Ab (clone JS-81, BD Biosciences), anti-LDL-R Ab (clone C7, Millipore), anti-EGFR Ab (clone LA1, Millipore) or rabbit polyclonal anti-SRB1 Ab (Novus Biologicals), at 4° C. for 1 h. Respective controls were mouse IgG1 or polyclonal rabbit IgG. After washing, cells were further incubated with fluorescein isothiocyanate (FITC)-conjugated secondary Ab (Jackson ImmunoResearch Laboratories, PA, USA) and analyzed by Cell Quanta™ SC High Resolution Flow cytometry (Beckman Coulter Fullerton, Calif., USA). To block cell surface molecules, 2×10$^5$ hADSC (adherent in wells) were pretreated with 1 ml serum-free K-medium containing indicated doses (1-100 μg/ml) of antibodies at 37° C. Treatment with respective isotype antibodies were used as a control. After 1 h, undiluted HCV(+) serum was added into the Eppendorf tubes to make MOI 0.2 for 3h-incubation in the presence of antibodies. Afterwards, cells were washed and plated in 6-cm petri dishes for continuous culture. For ApoE blockade, various concentrations of anti-ApoE antibody (clone E6D10) were added into the HCV(+) serum, as described[14], for 1 h at room temperature before 3 h-incubation with hADSC. Supernatants and cells were collected after 21 days' continuous culture and RNAs were extracted to quantify viral 5'-UTR transcripts. In separate experiments, hADSC in wells were pretreated with indicated doses of IFNα (Sigma-Aldrich, MO, USA) for 16 h in K medium in triplicates, before exposure to HCV(+) serum of genotype 1a, 1b, 2a and 2b. After 21 days, 5'-UTR transcripts in cell lysates were quantified by qRT-PCR, and results were calculated as fraction inhibition in comparison to cells treated with vehicle (PBS) controls.

RNA Extraction for RT-PCR of miR-122

Primers for RT-PCR of miR-122 was prepared and performed as described[39]. Total RNAs from cells were isolated with RNA extraction reagent REzol™ C&T (Protech, Taipei, Taiwan). To determine miR-122 levels, we transcribed reversely the extracted RNAs using the TaqMan MicroRNA Reverse Transcriptionas kit (Applied Biosystems), and cDNA was used as the templates for real-time PCR analysis with the TaqMan MicroRNA Assay for miR-122.

Synthetic siRNAs and Gene Silencing siRNA specific for occludin and claudin-1 were synthesized by Dharmacon as described[15,40,41]. Their respective target sequences are UAACAUUAGGACCUUAGAA (claudin-1) and GUGAAGAGUACAUGGCUGC (occludin). NPC1L1 were prepared as described[16], and siRNA for DGAT-1 was prepared as described[19]. Specific siRNAs were transfected into hADSC in wells of 6-well cell plates using Xfect transfection reagent (Clontech). HCV infection was carried out by incubating siRNA-transfected cells with HCVser at 37° C. for 3 h and then HCVser was washed off with PBS. Cells at 48 h post-transfection were lysed for RT-PCR to determine the degree of gene silencing, as described[15,19,40,41]. Cell lysates and supernatants of HCVser-infected hADSC were harvested after 21 days' culture for qRT-PCR of 5'-UTR.

JFH1/HCVcc and Huh7.5 Cells

Huh7.5 cells were cultured in DMEM (Invitrogen) containing 10% heat-inactivated fetal calf serum (Invitrogen) and 0.1 mM non-essential amino acids (Invitrogen). In vitro genomic JFH-1 RNA was transcribed and delivered to cells by electroporation as previously described[42]. Transfected cells were then transferred to complete DMEM and passaged every 3-4 days. In usual practice, the conditioned media from cells transfected with full-length JFH1 cDNA were clarified by centrifugation (3,000×g) for 10 min and sterile-filtered (0.2 μm cellulose acetate, Millipore) before use. For longer term storage, HCVcc was aliquoted and stored at −80° C. Virus was concentrated by addition of one-fourth volume sterile-filtered 40% (w/v) polyethylene glycol-8000 in PBS for overnight incubation at 4° C. Virus precipitates were collected by centrifugation (8,000×g, 15 min) and resuspended in PBS, as described[43].

Drug Inhibition Assay

Anti-viral drugs ribavirin, cyclosporin A, and IFNα were all from Sigma-Aldrich. Telaprevir was from Selleck Chemicals, MA, USA. Graded doses of ribavirin, telaprevir, or cyclosporin A were added in the medium of HCVser-infected hADSC in petri dishes on day 0 and cultured for 21 days. For IFNα treatment, hADSC were pretreated with indicated doses of IFNα for 16 h before incubation with HCVser. Viral 5'-UTR transcripts of the cell lysates were then quantified and calculated as fraction inhibition in comparison to cells treated with vehicle control. The vehicle controls were PBS for ribavirin and IFNα, and 0.1% DMSO for cyclosporin A and telaprevir.

Buoyant Density of HCVser, HCVadsc and HCVcc

The medium of HCVcc and HCVadsc was concentrated by PEG-8000 as described previously. All samples were re-suspended in 500 μl of serum-free medium and layered onto continuous iodixanol (OptiPrep, Axis-Shield, Norway) density gradients from 10% to 40% iodixanol (0.5 ml each) prepared with a solution containing 10 mM Hepes (pH 7.55), 150 mM NaCl, and 0.02% BSA, as described previously[44]. Gradients were ultracentrifuged at 40,000 rpm for 6 hours at 4° C. in an SW-41 rotor (Beckman Coulter). After ultracentrifugation, 17 fractions were collected from the tops of the gradients (each fraction contained 500 ul). Finally, total RNA was isolated from each fraction using QIAamp® Viral RNA Mini Kit (QIAGEN, Basle, Switzerland). RNA was used for HCV RNA detection by quantitative RT-PCR.

Determination of ApoB, ApoE and Cholesterol

Quantikine® ELISA Human Apolipoprotein B/ApoB Immunoassay kit and Quantikine® ELISA Human Apolipoprotein E/ApoE Immunoassay kit (R&D Systems) were used to detect ApoB and ApoE expression according the manufacturer's description. The cholesterol of HDL and LDL/VLDL were detected by HDL and LDL/VLDL Cholesterol Assay Kit (Abcam). The expression levels of ApoB, ApoE and cholesterol of HDL and LDL/VLDL in different fractions of buoyant density were normalized to copies.

Infection of Human Primary Hepatocytes (PHH) with HCVser or HCVadsc

Fresh non-tumoral liver tissues were taken from liver specimens surgically resected for HCV-related or -unrelated hepatocellular carcinoma, and PHH were isolated and cultured as described[45]. PHH were plated for 3 days to allow cell attachment onto the collagen I-coated 6-well plates. On day 4, cells were gently washed and cultured in Arginine-free Williams E media (Invitrogen, CA, USA) mixed with HCVser or its corresponding d21 hADSC-propagated HCV (+) supernatants (which contained 1×10$^4$ HCV 5'-UTR copies) in a final volume of 0.5 ml for 3 hours. After infection, cells were washed and further cultured in 1 ml of media with replacement of fresh medium every day until d5 post-infection. Cells were then lysed for RNA extraction for RT-PCR of 5'-UTR.

Example 1 hADSC are Targeted by HCV In Vivo

Clinically, an interesting feature of HCV infection is that HCV(+) patients may have excessive fat accumulation in the chronically infected liver, i.e., hepatic steatosis[46,47], and the severity of hepatic steatosis appears to correlate with the rate of liver fibrosis[48]. Recent studies also illustrate that HCV RNA replication can be stimulated by increasing the availability of saturated fatty acids, and is inhibited by polyunsaturated fatty acids or inhibitors of fatty acid synthesis[49,50]. These findings suggest that fat metabolism plays an important role in the life cycle of HCV. We therefore hypothesized that cellular components of fatty tissues might be implicated in HCV infection in vivo.

To test our hypothesis, we harvested subcutaneous fatty tissues from HCV-infected or -uninfected individuals (Table 1) and extracted RNAs for RT-PCT of HCV-specific 5'-UTR transcripts, using HCVser genotype 1b (HCVser-1b) as a positive control.

TABLE 1

A. HCV(+) donors for subcutaneous fatty tissues and liver tissues.
All patients received laparotomy for surgical resection of hepatocellular carcinoma. Fatty tissues [~(2-2.5 cm)$^3$] were harvested from the surgical wounds (laparotomy), and the liver tissues were harvested from the non-tumoral part (away from the lesion) of the resected liver. The patient number was the same as indicated in the FIG. 1F.

| Patient number | Age(y/o)/sex | HCV genotype | Serum HCV load (copies/ml) |
|---|---|---|---|
| 1 | 48/M | 1b | $1.6 \times 10^7$ |
| 2 | 71/M | 1b | $3.1 \times 10^6$ |
| 3 | 56/F | 2a | $2.9 \times 10^5$ |
| 4 | 51/M | 1a | $5.7 \times 10^6$ |

Note:
Samples of patients 1-3 were used in FIG. 1A-E, and samples of patients 1-4 were used in FIG. 1F. The sample size of the patient 4 was smaller [~(0.6-1.3 cm)$^3$] than requested, so the isolated adherent SVF cells of this sample was used only for the prolonged culture experiment (in FIG. 1F).

B. Donors for HCV(−) liver tissues. Patients were victims of HBV-related or non-B non-C hepatocecllular carcinoma and received liver resection.

| Patient number | Age(y/o)/sex | Hepatitis profile |
|---|---|---|
| 1 | 59/M | HBV(+), HCV(−) |
| 2 | 66/M | HBV(+), HCV(−) |
| 3 | 42/M | HBV(−), HCV(−) |

Note:
The diagnosis of hepatitis virus infection in Tables 1A and 1B was made at the time when the hepatocellular carcinoma was diagnosed, and anti-viral treatment was given after tissue harvesting.

Figure 5:
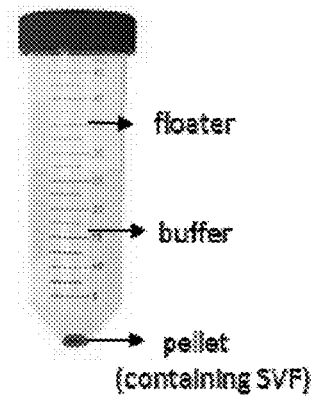
FIG. 5. Separation of the homogenates of human fatty tissues into different layers by centrifugation. Fatty tissues of HCV(+) individuals were centrifuged and separated into layers of floater, buffer and cell pellet (left panel), as described[9]. The floating population contains mature adipocytes. The cell pellet was collected and treated with RBC lytic buffer to lyse the erythrocytes to harvest the stromal vascular fraction (SVF) cells, and SVF cells were subjected to immune-selection of DLK-1+ human adipogenic stem cells (hADSC), which can be regarded as primary (passage-0) hADSC.

Interestingly, fatty tissues of HCV(+) individuals (patients no. 1-3 of genotype 1b or 2a, Table 1) contained viral 5'-UTR (223 bp, FIG. 1A), in contrast to those of HCV(−) individuals. To exclude possible contamination from the blood and to define the cell source expressing viral transcripts, we fractionated fatty tissues by centrifugation, as described[12,13,33], into a floating layer (floater) at the top which contained mature adipocytes, a buffer layer in the middle, and a sedimented cell pellet at the bottom (FIG. 5). The cell pellet was collected and further treated with RBC lytic buffer to lyse the erythrocytes to harvest the stromal vascular fraction (SVF) cells. RNAs were then separately extracted from the floater layer and RBC-lysed SVF cells, but little RNA could be extracted from the buffer layer (data not shown). RT-PCR demonstrated that while no viral 5'-UTR was detected in the floater layer, viral transcripts were detected in SVF cells (left panel, FIG. 1B).

Figure 1:
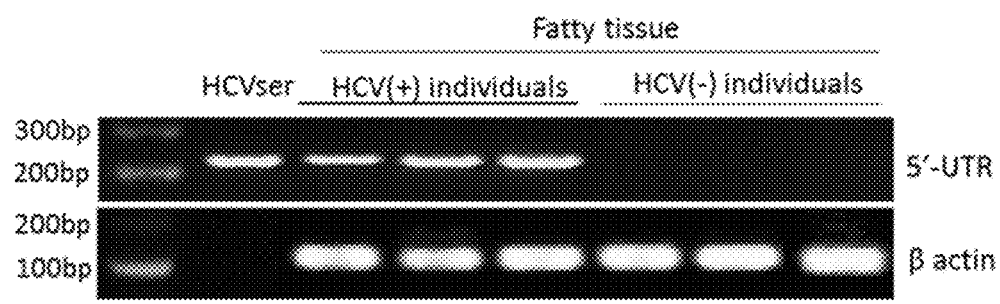
FIG. 1. Human adipose-derived DLK-1$^+$ stem cells are targeted by HCV in vivo. (A) Fatty tissues of 3 HCV(+) individuals (Table 1) were harvested from surgical wounds and RNAs were extracted for RT-PCR of HCV-specific 5'-UTR (223 bp). Fatty tissues harvested from 3 HCV(−) individuals were also studied in parallel for comparison, and HCV(+) serum was used as a positive control. (B) Fatty tissues of HCV(+) individuals were minced, homogenated and centrifuged into layers of floater, buffer and cell pellet. Erythrocytes of the cell pellet were further lysed to harvest SVF. RNAs were extracted from each cell population and subjected to RT-PCR for 5'-UTR. Viral transcripts were detected in SVF cells, not in the floater (left panel). SVF cells were further immune-separated into DLK-1$^-$ and DLK-1$^+$ cells and RNAs were extracted separately for RT-PCR. Viral transcripts were present in DLK-1$^+$ cells, not in DLK-1$^-$ cells (right panel). Data are representative of 3 experiments using cells from 3 HCV(+) donors. (C) RNAs of DLK-1$^-$ and DLK-1$^+$ cells isolated from 3 HCV-infected individuals were extracted for RT-PCR of HCV negative strand RNA. Primary human hepatocytes (PHH) isolated from an HCV(+) individual were used as a positive control. (D) DLK-1$^-$ (panels b & e) and DLK-1$^+$ cells (panels c & f), isolated from HCV(−) and HCV(+) individuals, were spun onto cytospin slides for immunocytochemistry for viral NS5 (brown label in c) and hematoxylin staining (blue label at nuclei). Staining of the unfractionated SVF cells with mouse IgG1 control antibody (panel a & d) was used as negative controls. Data are representative of samples from 3 HCV(+) and 3 HCV(−) donors. (E) Fatty tissues from HCV(+) or HCV(−) individuals were sequentially stained for DLK-1 (red label, arrows in panels b, c, & h) and for viral NS5 (brown label, arrows in panels e & f) and hematoxylin (blue label, panels d-f and i-j) on the same sections. In HCV(+) fatty tissues, DLK-1$^+$ cells (red label, arrows, panels b & c) co-expressed NS5 Ag (brown label, arrows, panels e & f). In HCV(−) fatty tissues, DLK-1$^+$ cells (panel h, arrows) did not express NS5 (panel j, arrows; h vs j). Staining with rabbit IgG (panels a & g) or mouse IgG1 (panels d & i) was used as negative controls. Panels b, e and c, f were from separate donors. Data are representative of 3 HCV(+) and 3 HCV(−) donors. (F) DLK-1$^+$ cells isolated from fatty tissues of 4 HCV(+) individuals were ex vivo cultured for 49 days, and the supernatants were collected every 7 days for qRT-PCR of 5'-UTR. Data are expressed as mean±SD from triplicates for each time point.
Figure 1:
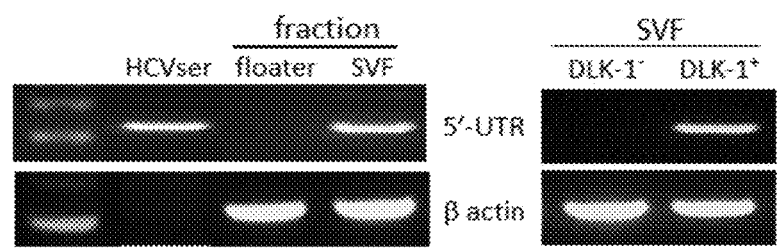
Figure 1:
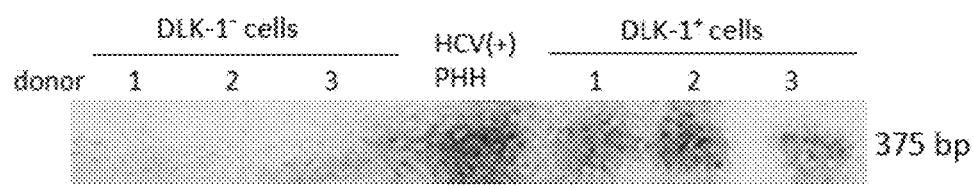
Figure 1:
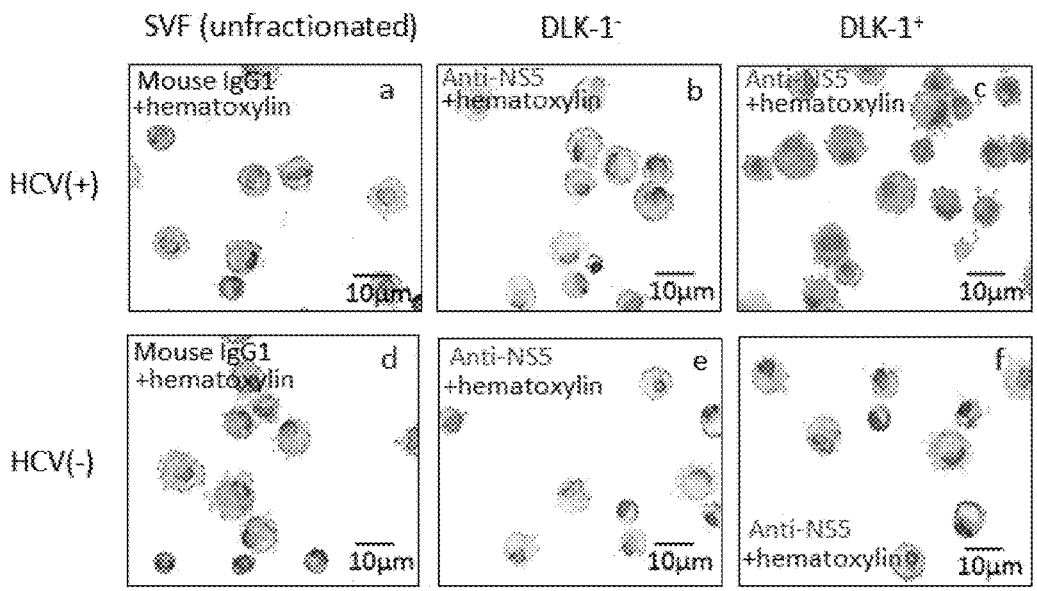
Figure 1:
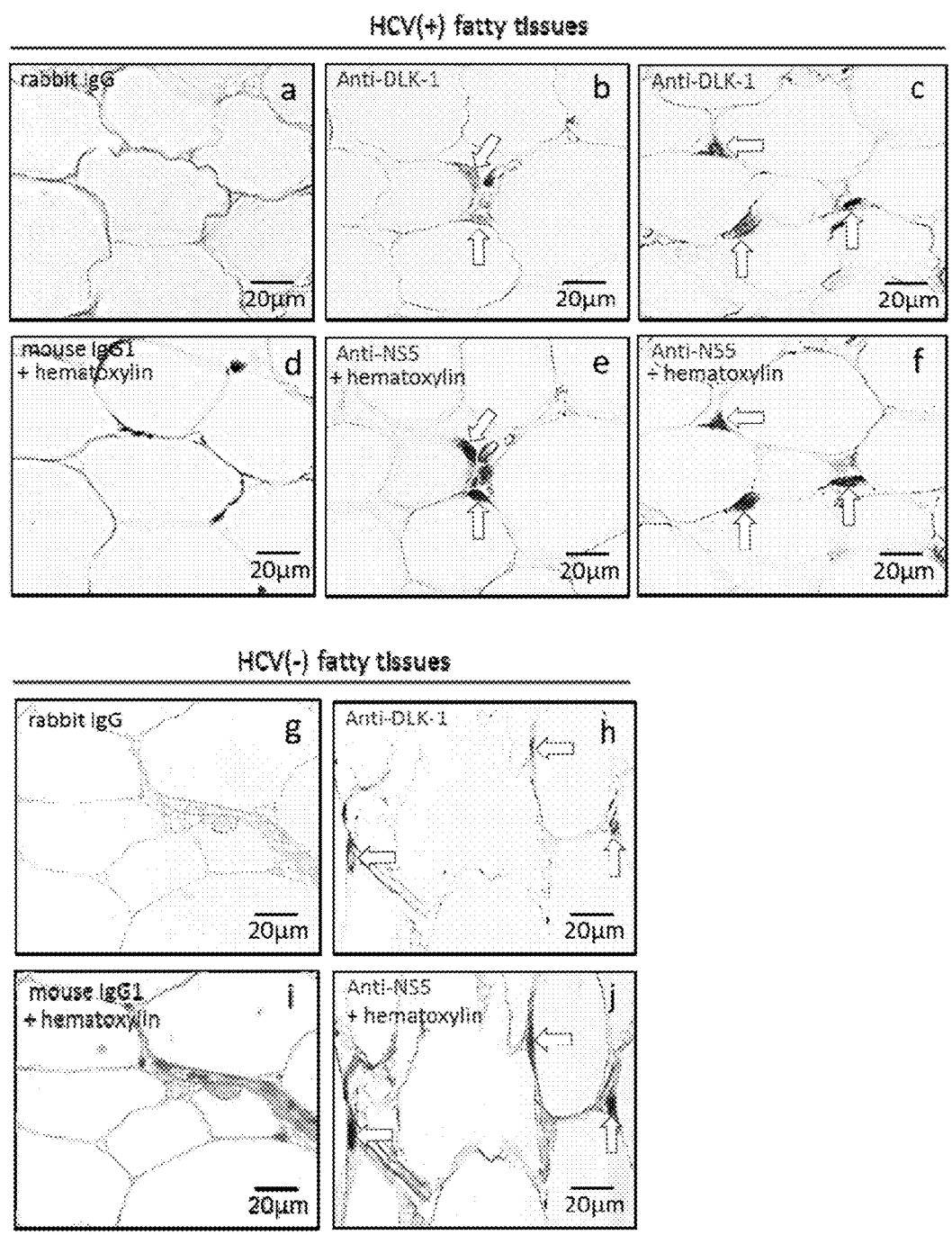
Figure 1:
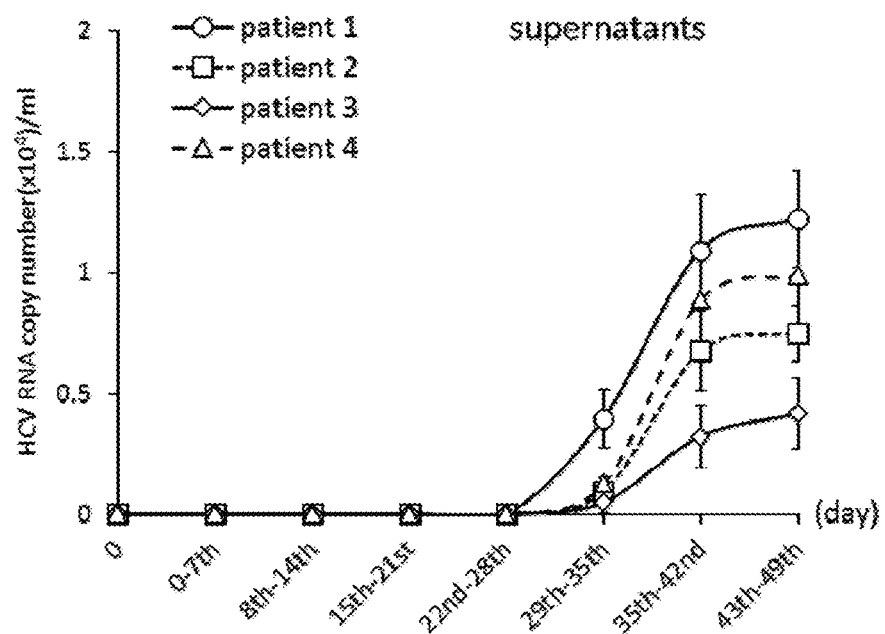
Figure 6:
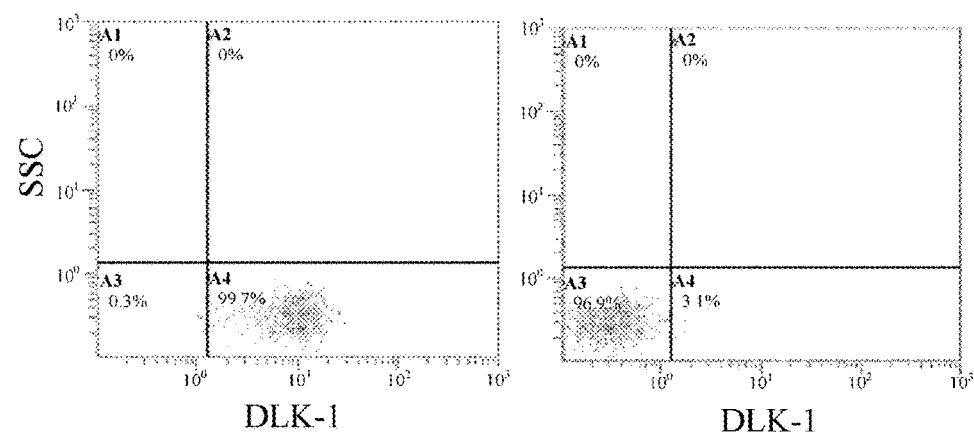
FIG. 6. Purity of the selected fractions and RT PCR for DLK-1. (A) The percentage of DLK-1+ cells in the DLK-1+ (left) and DLK-1− (right) fractions was determined by using a MoFlo XDP flow cytometer (Becton Coulter, CA, USA) and analyzed with Submit software. Elimination of 99.5% autofluorescence of the DLK-1+ and DLK-1− fractions was used to set gates for determining positively stained cells in each fraction. Similar results were obtained using unfractionated SVF cells incubated with the isotype control antibody (rabbit IgG). Data are representative of 6 experiments. (B) RNAs were extracted from the unfractionated SVF cells, selected DLK-1− and DLK-1+ cells[10] and subjected to RT-PCR for DLK-1 (primers as described[11]). DLK-1− cells expressed little DLK-1 mRNA, in contrast to the abundant expression in DLK-1+ cells. Data are representative of 4 experiments.
Figure 6:
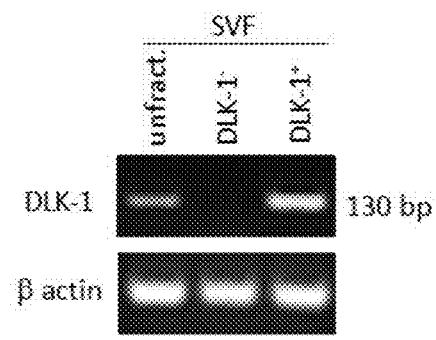
Figure 7:
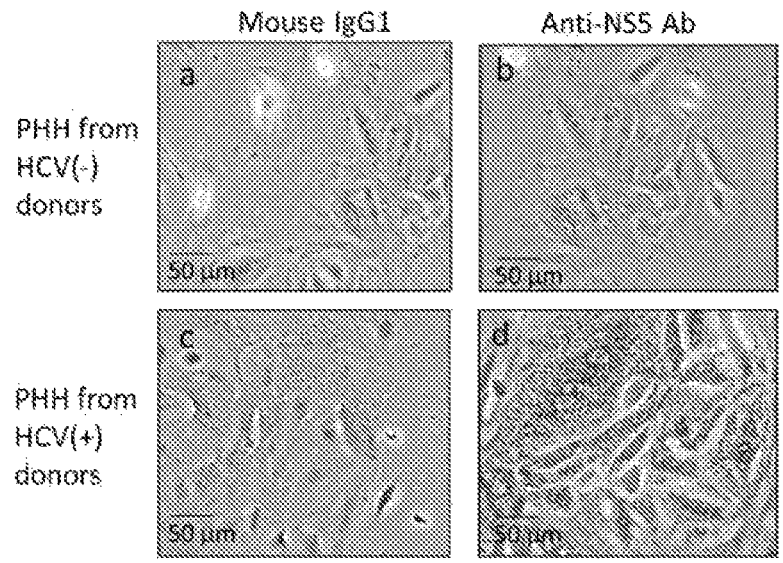
FIG. 7. HCV-infected primary human hepatocytes (PHH) expressed NS5 antigen. PHH were harvested from HCV(−) or HCV(+) donors (panels a & b, and c & d, respectively) and seeded in collagen-I coated wells for culture. As a control experiment, we examined the specificity of NS5 staining on primary human hepatocytes (PHH; seeding number $1 \times 10^4$ cells/well) freshly isolated from HCV(+) or HCV(−) donors and cultured in Arginine-free Williams E media (Invitrogen, CA, USA). On day 9, cells were washed and subjected to immunocytochemistry in the wells, employing methods similarly described for staining the cells on cytospin slides (see "Methods"). Data are representative of 3 experiments using PHH from 3 HCV(+) and 3 HCV(−) donors.

We next positively selected DLK-1$^+$ cells from SVF cells by immuno-magnetic beads as described[10], and flow cytometry analysis confirmed >99.7% of the positively selected cells expressed DLK-1 (FIG. 6). RNAs were subsequently extracted from DLK-1$^+$ and DLK-1$^-$ cells separately for RT-PCR, which confirmed that viral transcripts were present in DLK-1$^+$ cells, but not in DLK-1$^-$ cells (right panel, FIG. 1B). We also performed RT-PCR for HCV-specific negative strand RNA[51], using RNA extracted from HCV(+) primary human hepatocytes (PHH) as a positive control. Data confirmed that HCV replication intermediates were present in DLK-1$^+$ cells, but not in DLK-1$^-$ cells, of all 3 HCV(+) donors (375 bp; FIG. 1C). DLK-1$^+$ and DLK-1$^-$ cells were also separately spun onto cytospin slides for immunocytochemistry with mouse anti-HCV NS5 antibody (clone BGN/1246/5G7) and hematoxylin (to delineate cell nuclei). Cells isolated from HCV(−) individuals were also stained for comparison. Consistent with the mRNA expression of 5'-UTR, DLK-1$^+$ cells isolated from HCV(+) donors expressed NS5 antigen (brown label, panel c, FIG. 1E), whereas NS5 expression of DLK-1$^-$ cells was close to the background, regardless of HCV infection status (panel b & e). Staining of unfractionated HCV(+) or HCV(−) SVF cells with isotype antibody (mouse IgG1) was used as controls (panels a & d, FIG. 1E). Hematoxylin staining (blue label) confirmed that NS5$^+$ cells were genuine nucleated cells (panel c, FIG. 1E), rather than cellular debris. The specificity of anti-NS5 antibody has been verified in the staining of HCV(+) PHH (FIG. 7).

For in vivo validation, we performed immunohistochemistry on the subcutaneous fatty tissues harvested from HCV-infected and -uninfected individuals. Tissue sections were first stained with anti-DLK-1 Ab. After immersion and washing with PBS, the same sections were stained with anti-NS5 Ab and hematoxylin. Results showed that DLK-1 was detected in adipose tissues harvested from both HCV-infected and -uninfected individuals (red label, white arrows, panels b & c, and h, respectively, FIG. 1E), in locations similarly described in mouse fatty tissues[52]. Furthermore, NS5$^+$ cells were visualized in HCV(+) fatty tissues (brown label, white arrows, panels e & f, FIG. 1E), but not in HCV(−) samples (panel j). Notably, viral NS5 was co-localized with DLK-1 expression in HCV(+) samples (panels b vs e and c vs f, FIG. 1E; b & e and c & g were from separate donors; also see FIG. 8). In all sections examined, about 0-4 DLK-1$^+$NS5$^+$ cells were found per high magnification field (400×) in HCV(+) fatty tissues.

To determine whether hADSC of HCV(+) individuals produced viruses, we cultured DLK-1$^+$ cells isolated from HCV(+) patients and quantified the viral copy number in supernatants every 7 days. Interestingly, while few viral transcripts were detected in the first 4 weeks, they became detectable in supernatants from d28-d35 onwards and the copy number increased time-dependently (to d49; FIG. 1F). Furthermore, the amount of viral transcripts upon prolonged culture seemingly correlated with serum viral titers of the respective patients from whom the cells were isolated (FIG. 1F and Table 1).

Collectively, our data provide evidence that hADSC are targeted by HCV in vivo.

Example 2 Naïve HCV(−) hADSC are Susceptible to HCVser Infection and Replication In Vitro To examine if naïve HCV(−) hADSC were susceptible to HCVser infection and replication in vitro, we prepared hADSC from HCV(−) individuals and passaged them in culture. Passage-3 (p-3) or p-4 cells in suspension (in Eppendorf tubes) were incubated with HCVser (Table 2) at 0.2 moi in a final volume of 1 ml (i.e., $1\times10^5$ 5'-UTR copy number versus $5\times10^5$ hADSC cells).

TABLE 2

HCV genotype and 5'-UTR copy numbers of HCV(+) serum used in this study. All patients had no evidence for infection of HIV or hepatitis B virus. They also had no signs of acute infectious diseases. Sera were collected from September 2011 to February 2014 and used immediately or stored in −80° C. until use. Sera of patient no. 1-5 were used in FIG. 2A-D, and the remaining were used in FIG. 2E-F, FIG. 3 and FIG. 4.

| Patient number | Genotype | 5'-UTR copy number/ml |
| --- | --- | --- |
| 1 | 1b | 176,554 |
| 2 | 1b | 489,226 |
| 3 | 1b | 125,117 |
| 4 | 2b | 22,338 |
| 5 | 2b | 269,274 |
| 6 | 1b | 2,204,192 |
| 7 | 2a | 10,235,072 |
| 8 | 1b | 3,416,616 |
| 9 | 2b | 2,113,496 |
| 10 | 2b | 155,064 |
| 11 | 1b | 408,572 |
| 12 | 1a | 695,868 |
| 13 | 1b | 3,652,720 |
| 14 | 1a | 582,610 |
| 15 | 1b | 10,169,980 |
| 16 | 1b | 2,603,320 |
| 17 | 1b | 576,728 |
| 18 | 2a + 2b | 7,357,744 |
| 19 | 2b | 53,428,656 |
| 20 | 2a | 9,266,436 |
| 21 | 1b | 744,228 |
| 22 | 1b | 60,154,272 |
| 23 | 1b | 335,460 |
| 24 | 2a | 74,090 |
| 25 | 1a | 9,179,112 |
| 26 | 2a + 2b | 67,012 |
| 27 | 2b | 1,455,144 |
| 28 | 2a | 632,901 |
| 29 | 2a | 46,793,192 |

After 3 h, cells were washed and transferred to 6-cm petri dishes for culture, with medium replacement every 7 days, and the supernatants and cell lysates were harvested on day 7, 14, 21 and 28 for RNA extraction (protocol in FIG. 9). As a control for HCVser infectivity, HCV(−) PHH isolated from non-tumor liver tissues (as described[45] and Table 1) were plated in wells for 3 days to allow cell attachment, and then incubated with HCVser or HCV(−) control serum (blood type AB) for 3 h on day 4; after washing, PHH were further cultured for 5 days before cellular RNA extraction. Results showed that PHH exposed to HCVser indeed expressed viral 5'UTR (labeled as "+", left, FIG. 2A), while cells exposed to HCV(−) control serum did not (labeled as "−").

In post-infection culture, viral transcripts could not be detected in either d7-supernatants or d7-cell lysates, but became detectable in d14-cell lysates in all experiments and also in the supernatants in 10 out of 18 experiments (right, FIG. 2A; totally 18 experiments using hADSC from 8 donors, Table 3). Meanwhile, 5'-UTR was consistently detected in both d21 and d28 supernatants, as well as in cell lysates, of all experiments (right, FIG. 2A).

We also examined HCV-specific negative strand RNA, and results confirmed that both d14 and d28 HCVser-1b infected hADSC expressed replication intermediates, which were absent in supernatants, as expected (FIG. 2B). PHH isolated from a HCV-infected patient was used as a positive control.

For further confirmation, infected hADSC were spun onto glass slides for sequential immunocytochemistry study. Cells were first stained with anti-DLK-1 antibody, followed by staining with anti-NS5 antibody and hematoxylin on the same sections. Results showed that d14 HCVser-1b infected hADSC indeed expressed DLK-1 (red label, panel b, FIG. 2C), and consistent with RT-PCR findings, they also expressed NS5 (brown label, panel d, FIG. 2C), in contrast to control serum-pulsed hADSC that expressed DLK-1 (panel f) but no NS5 (panel h). Staining with isotype antibodies rabbit IgG and mouse IgG1 (controls for anti-DLK-1 and anti-NS5 antibody, respectively) demonstrated background colors (panels a & c, and e & g, respectively). Because virtually all HCVser-infected DLK-1$^+$ cells expressed NS5 (panels b vs d), the permissiveness of hADSC to infection of clinical isolates appeared to be a generalized property, rather than being restricted to just a subset(s) of cells.

D14 and d21 HCVser-hADSC were also studied by transmission electron micrography. Compared with hADSC exposed to HCV(−) control serum (panels a & d, FIG. 2D), viral particles of ≈50-60 nm in diameter could be visualized outside (white arrows in inlets, panels b & e, FIG. 2D) and inside the hADSC (white arrows in inlets, panels c & f, FIG. 2D). Viral particles identified outside the cells were wrapped in membranous vesicles composed of double membranes (yellow arrow and magnified in the inlet, panel b) or an electron-dense membranous structure (yellow arrow and magnified in the inlet, panel e). In contrast, viral particles found inside the cells were either in a free form without membranous wrapping (yellow square and magnified in the inlet, panel c; viral particles indicated by white arrows) or surrounded by multiple circular concentric membranes ("onion-shaped", yellow square and magnified in the inlet, panel f, viral particles indicated by white arrows).

In addition to infecting hADSC in suspension (FIG. 2, A-D), we also infected hADSC in adherence by plating them in 6-cm petri dishes for 1 day, and then pulsed the cells with HCVser at 0.5 moi ($1\times10^5$ 5'-UTR copies versus $2\times10^5$ hADSC cells) in a final volume of 2 ml for 3 h. After gentle washing, cells were cultured in 5 ml of fresh medium with medium replacement every 7 days (FIG. 10). RNAs of the supernatants and cell lysates were extracted on days 7, 14, 21 and 28 and subjected to qRT-PCR. Results revealed that viral transcripts were consistently detectable in cell lysates at day 7, despite their absence in supernatants (left vs right panel, FIG. 2E). Furthermore, viral copies in cell lysates increased most remarkably in the $2^{nd}$ week (left panel, FIG.

2E), whereas the increase in supernatants was most noticeable with a one-week lag, i.e., the 3$^{rd}$ week (right panel, FIG. 2E).

To measure total viral copies produced by this system, we cultured HCVser-infected hADSC continuously without medium replacement (FIG. 10) and collected the supernatants at the end of indicated culture periods. qRT-PCR confirmed that the most substantial viral release (into supernatants) occurred in the 3$^{rd}$ week with a total copy number of ~3×10$^5$/ml after 28 days' culture (FIG. 2F).

TABLE 3

Characteristics of donors for naive hADSC

| | Donor | | | | | | | |
|---|---|---|---|---|---|---|---|---|
| | 1 | 2 | 3 | 4 | 5 | 6 | 7 | 8 |
| age (yr)/sex | 40/F | 41/F | 52/F | 55/F | 49/F | 60/F | 36/M | 27/M |
| disease | breast cancer for mastectomy and breast reconstruction | | | | | | Obesity | |
| hADSC origin | lipectomized fatty tissues from TRAM flap* | | | | | | liposuction materials from abdominal wall or hips/thighs | |

*TRAM flap: transverse rectus abdominus myocutaneous flap

Example 3 hADSC-Produced Virions are Genuine "Virions" Exhibiting Biological Properties of Clinical Isolates To examine the infectivity of hADSC-produced virions (labeled as "HCVadsc"), we infected p2 hADSC of "donor 1" with HCVser-1b and collected supernatants on day 21 (labeled as "HCVadsc(1)"). After filtration through a 0.22-μm pore filter, HCVadsc(1) was used to infect hADSC of "donor 2" to make HCVadsc(2), which was subsequently used to infect hADSC of "donor 3". Results confirmed that HCVadsc possessed infectivity towards naive hADSC of different donors, with a relatively consistent replication efficiency as seen in the initial infection by HCVser (FIG. 3A). Similar observations were also made for HCVadsc derived from supernatants of hADSC initially infected with HCVser-1a, -2a and -2b (data not shown).

We next studied the permissiveness of hADSC at different passage number by infecting p2, p6, p9 and p15 hADSC with HCVser-1b and measured viral copies after 21 days' continuous culture. Results showed that in contrast to p2 and p6 cells, the p9 and p15 hADSC had very low levels of viral transcripts in both supernatants and cell lysates (left and right panels, respectively, FIG. 3B). Similar observations were made for infection with HCVser-1a and -2a (FIG. 11). In experiments to define the DLK-1 expression of naive [HCV(−)] hADSC, we found that DLK-1 expression was detectable from p0 to p6, but reduced at p9 and was undetectable at p15 (FIG. 3C), following a similar trend as noted for the permissiveness of HCV infection.

Moreover, hADSC appear to have no preference over infection of genotype 1 or 2 (FIG. 3B & FIG. 11). To examine this further, we infected p5 hADSC with HCVser of mixed genotype 2a+2b and collected cells for RT-PCR to detect mRNAs encoding the genotype-specific core antigens. Indeed, mixed 2a+2b HCVser per se (as a positive control) expressed mRNAs encoding core antigens of both genotype 2a and 2b (174 and 123 bp, lane "P", left and right panels, respectively; FIG. 3D), which were also detected in d21 and d56 cell lysates of genotype 2a+2b infected hADSC. In this experiment, cells pulsed by HCV(−) control serum were used as a negative control (labeled as "N"). Therefore, permissiveness of hADSC for infection by clinical isolates is cross-genotypic, at least for genotype 1a, 1b, 2a, and 2b.

Host factors including tetraspanin CD81, LDL-R, SR-B1, epithelial growth factor receptor (EGFR), Apolipoprotein (Apo) E, occludin, claudin-1, the Niemann-Pick C1-like 1 (NPC1L1) cholesterol absorption receptor and diacylglycerol acetyltransferase-1 (DGAT-1) have been shown to mediate HCV infection/replication in human hepatocytes or hepatoma cell lines[15,16,19,53-58], either at the viral attachment or post-attachment step. We examined the expression of these molecules in hADSC by flow cytometry or RT-PCR.

Flow cytometry revealed that p0 (i.e., adherent SVF cells), p2 and p6 hADSC clearly expressed CD81, LDL-R, SR-B1, and EGFR (FIG. 3E). RT-PCR also confirmed the expression of mRNA encoding occludin (OCLN), claudin-1 (CLDN1) and NPC1L1, but not miR-122 (left, FIG. 3F). In contrast, miR-122 was abundantly expressed in Huh7.5 hepatoma cells (~60 folds higher than hADSC) and was even more abundant in PHI-1 (~2000 folds higher; right, FIG. 3F).

To determine the role of these molecules, we pre-treated p2 hADSC with graded doses of monoclonal Ab against CD81 (clone JS-81), LDL-R (clone C7), EGFR (clone LA-1), or polyclonal Ab against SR-B1, for 1 h before pulse by HCVser-1b. For ApoE blockade, various concentrations of anti-ApoE antibody (clone E6D10) were added to the HCV(+) serum for 1 h at room temperature before use for infection, as described[14]. Quantification of viral transcripts in 21 days' supernatants showed that blockade of CD81, LDL-R, SR-B1, EGFR and also neutralization of ApoE in the HCV(+) serum significantly reduced the amount of viral copies in a dose-dependent manner; meanwhile, treatment per se did not significantly affect the cell viability (FIG. 3G). A similar dose-response reduction in viral copies of the cell lysates was also noticed (FIG. 12).

We also transfected p2 hADSC, prior to infection by HCVser-1b, with siRNA specific for occludin or claudin-1, or in separate experiments for NPC1L1, as described[15,16]. We have also examined the role of DGAT-1, a molecule required for the trafficking of HCV nucleocapsid core to lipid droplets and important for HCV production in hepatoma cell lines[19]. RT-PCR confirmed the effects of mRNA knock-down (FIG. 13), which subsequently reduced the viral copies in supernatants (FIG. 3H) and cell lysates (FIG. 13) after 21 day's culture.

Finally, we examined the inhibitory effect of anti-viral drugs. Cells at p4-5 were plated in wells and exposed to HCVser-1b, and graded concentrations of anti-viral drugs, including ribavirin, telaprevir, or cyclosporine A (a cyclophilin A inhibitor), were added in the culture medium. For IFNα treatment, hADSC were pretreated with indicated doses of IFNα for 16 h before incubation with HCVser. Viral transcripts in 21 days' cell lysates were then determined and calculated as fraction inhibition in comparison to cells treated with vehicle control. Results demonstrated that HCV replication was inhibited in a dose-responsive manner by ribavirin, telaprevir, cyclosporine A and IFNα (FIG. 3I). The expression of cyclophilin A in p0, p2 and p6 hADSC had been confirmed in our preliminary experiments (FIG. 14). Therefore, HCVadsc are genuine "virions" exhibiting biological properties of clinical isolates.

Example 4 hADSC are an In Vivo HCV Reservoir Permitting Complete HCV Replication To characterize physical properties of HCVadsc, we compared the buoyant density profiles of HCVser, HCVcc and HCVadsc by equilibrium centrifugation, as described[43]. All viruses studied were derived from genotype 2a. Consistent with previous reports[43,59,60], HCVser had a high amount of RNA at fractions of lower densities 1.039 (fraction 2) and 1.080 (fraction 7), whereas that of HCVcc peaked at 1.132 (fraction 13; FIG. 4A). The highest amount of RNA for HCVadsc was seen at density 1.080 (fraction 7), followed by two peaks at higher densities 1.124 and 1.156 (fraction 12 and 15). Of interest, the peak at 1.080 of HCVadsc was identical to that of HCVser (FIG. 4A). Therefore, the physical property of HCVadsc resembles the clinical isolates more than HCVcc.

We also determined the lipid and Apolipoprotein (Apo) profile of each major fraction, including HDL, VLDL/LDL, and ApoE and ApoB. HCVser appeared to have the highest total lipid amounts compared to HCVcc and HCVadsc (FIG. 15), which was not unexpected because the microenvironment for viral propagation was different (serum vs culture medium). Furthermore, when expressed as weight (ng) per viral copy, HCVcc fraction 13 had the lowest HDL and LDL/VLDL contents (FIG. 4B). Major fractions of HCVser also had the highest ApoE contents (in terms of pg/copy), followed by HCVadsc, and HCVcc fraction 13 had a barely detectable ApoE level (FIG. 4C). Thus, HCVadsc also exhibits more likeness to HCVser than to HCVcc in the viral particle-associated lipid contents. Interestingly, ApoB was not detected in any fraction of HCVadsc, implying that ApoB may not be required for infection in hADSC, as opposed to ApoE (FIG. 3G).

We also compared the infectivity of various viruses towards hADSC by infecting p2 hADSC with viral inoculum of JFH1/HCVcc, alongside with HCVser. HCVcc replication in Huh7.5 cells was performed in parallel as a control. We found that in contrast to the efficient replication of HCVcc in Huh7.5 cells (FIG. 16), HCVcc-infected hADSC produced few 5'-UTR transcripts in either supernatants or cell lysates after 14 days' or 21 days' culture (FIG. 4D), and HCVser infection of hADSC displayed similar replication kinetics as before (FIG. 4D vs 3A). The 21 days' supernatants of naive Huh7.5 and HCVcc-infected Huh7.5 cells, as well as those of HCVcc or HCVser infected hADSC, were also collected for RNA extraction and subjected to RT-PCR. Results confirmed that no viral transcripts were detected in HCVcc-infected hADSC supernatants (lane 3, FIG. 4E), in contrast to HCVcc infection of Huh7.5 and HCVser infection of hADSC (lane 2 and 4, respectively, FIG. 4E).

We next examined the infectivity of HCVadsc towards naive PHH. PHH were isolated from HCV(−) individuals as described[45] and cultured for 3 days (1×10⁴ cells/dish) to allow cell attachment, and subsequently exposed to HCVadsc prepared from 21 days' supernatants of HCVser-1b infected hADCS culture. Cellular RNAs were extracted 5 days post-infection for RT-PCR. Results showed that in contrast to infection by supernatants of control serum-pulsed hADSC (as a negative control, lane "1", FIG. 4F), HCVadsc-infected PHH indeed expressed viral 5'-UTR (labeled "2" & "3, FIG. 4F).

Finally, PHH from 3 different donors were prepared and seeded in wells as described previously. On day 4, cells were infected by HCV(−) control serum (from 3 different individuals), HCVser-1b (from 3 separate donors) and its corresponding HCVadsc. HCVser and the corresponding HCVadsc were paired to infect the same batch of PHH. The supernatants were collected 5 days post-infection and 5'-UTR copies were quantified. Exposure of PHH to HCV (−) control serum were used as negative controls. Results showed that infection of HCVser resulted in highly variable replication kinetics, as has been reported previously in PHH infection with clinical isolates[61]. Infection by HCVadsc also resulted in an increase of the viral titers, which were highly variable as in the case of HCVser infection (FIG. 4G). These findings confirmed the infectivity of HCVadsc towards hepatocytes.

In summary, hADSC are an in vivo HCV reservoir permitting complete HCV replication and represent a previously unrecognized venue for clinical HCV-host interaction. Moreover, hADSC are the first kind of non-hepatic primary cells that allow in vitro propagation of clinical HCV isolates, which may become a novel tool for deciphering HCV life cycle and facilitate the development of anti-viral strategies.

All publications and patents mentioned in the specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in cell culture, molecular biology, biochemistry, or related fields are intended to be within the scope of the appended claims

REFERENCES

1. Lindenbach, B. D. & Rice, C. M. Unravelling hepatitis C virus replication from genome to function. *Nature* 436, 933-938 (2005).
2. Scheel, T. K. & Rice, C. M. Understanding the hepatitis C virus life cycle paves the way for highly effective therapies. *Nature medicine* 19, 837-849 (2013).
3. Blackard, J. T., Kemmer, N. & Sherman, K. E. Extrahepatic replication of HCV: insights into clinical manifestations and biological consequences. *Hepatology* 44, 15-22 (2006).
4. Laporte, J., et al. Differential distribution and internal translation efficiency of hepatitis C virus quasispecies present in dendritic and liver cells. *Blood* 101, 52-57 (2003).
5. Wilkinson, J., Radkowski, M. & Laskus, T. Hepatitis C virus neuroinvasion: identification of infected cells. *Journal of virology* 83, 1312-1319 (2009).
6. Letendre, S., et al. Pathogenesis of hepatitis C virus coinfection in the brains of patients infected with HIV. *J Infect Dis* 196, 361-370 (2007).
7. Lohmann, V. & Bartenschlager, R. On the history of hepatitis C virus cell culture systems. *Journal of medicinal chemistry* 57, 1627-1642 (2014).
8. Yang, D., et al. Complete replication of hepatitis B virus and hepatitis C virus in a newly developed hepatoma cell line. *Proc Natl Acad Sci USA* 111, E1264-1273 (2014).
9. Bunnell, B. A., Flaat, M., Gagliardi, C., Patel, B. & Ripoll, C. Adipose-derived stem cells: isolation, expansion and differentiation. *Methods* 45, 115-120 (2008).
10. Oertel, M., et al. Purification of fetal liver stem/progenitor cells containing all the repopulation potential for normal adult rat liver. *Gastroenterology* 134, 823-832 (2008).
11. Abdallah, B. M., et al. Regulation of human skeletal stem cells differentiation by Dlk1/Pref-1. *Journal of bone and*

*mineral research: the official journal of the American Society for Bone and Mineral Research* 19, 841-852 (2004).

12. Yoshimura, K., et al. Characterization of freshly isolated and cultured cells derived from the fatty and fluid portions of liposuction aspirates. *J Cell Physiol* 208, 64-76 (2006).

13. Lin, S. D., Wang, K. H. & Kao, A. P. Engineered adipose tissue of predefined shape and dimensions from human adipose-derived mesenchymal stem cells. *Tissue Eng Part A* 14, 571-581 (2008).

14. Jammart, B., et al. Very-low-density lipoprotein (VLDL)-producing and hepatitis C virus-replicating HepG2 cells secrete no more lipoviroparticles than VLDL-deficient Huh7.5 cells. *Journal of virology* 87, 5065-5080 (2013).

15. Owen, D. M., Huang, H., Ye, J. & Gale, M., Jr. Apolipoprotein E on hepatitis C virion facilitates infection through interaction with low-density lipoprotein receptor. *Virology* 394, 99-108 (2009).

16. Sainz, B., Jr., et al. Identification of the Niemann-Pick C1-like 1 cholesterol absorption receptor as a new hepatitis C virus entry factor. *Nature medicine* 18, 281-285 (2012).

17. Dorner, M., et al. A genetically humanized mouse model for hepatitis C virus infection. *Nature* 474, 208-211 (2011).

18. Krapivner, S., et al. DGAT1 participates in the effect of HNF4A on hepatic secretion of triglyceride-rich lipoproteins. *Arterioscler Thromb Vasc Biol* 30, 962-967 (2010).

19. Herker, E., et al. Efficient hepatitis C virus particle formation requires diacylglycerol acyltransferase-1. *Nature medicine* 16, 1295-1298 (2010).

20. Kaul, A., et al. Essential role of cyclophilin A for hepatitis C virus replication and virus production and possible link to polyprotein cleavage kinetics. *PLoS Pathog* 5, e1000546 (2009).

21. Smas, C. M. & Sul, H. S. Pref-1, a protein containing EGF-like repeats, inhibits adipocyte differentiation. *Cell* 73, 725-734 (1993).

22. Lee, K., et al. Inhibition of adipogenesis and development of glucose intolerance by soluble preadipocyte factor-1 (Pref-1). *The Journal of clinical investigation* 111, 453-461 (2003).

23. Gesta, S., Tseng, Y. H. & Kahn, C. R. Developmental origin of fat: tracking obesity to its source. *Cell* 131, 242-256 (2007).

24. Wang, Y. & Sul, H. S. Pref-1 regulates mesenchymal cell commitment and differentiation through Sox9. *Cell Metab* 9, 287-302 (2009).

25. Gimble, J. M., Katz, A. J. & Bunnell, B. A. Adipose-derived stem cells for regenerative medicine. *Circulation research* 100, 1249-1260 (2007).

26. Mizuno, H., Tobita, M. & Uysal, A. C. Concise review: Adipose-derived stem cells as a novel tool for future regenerative medicine. *Stem Cells* 30, 804-810 (2012).

27. Parsons, C. H., Szomju, B. & Kedes, D. H. Susceptibility of human fetal mesenchymal stem cells to Kaposi sarcoma-associated herpesvirus. *Blood* 104, 2736-2738 (2004).

28. Avanzi, S., et al. Susceptibility of human placenta derived mesenchymal stromal/stem cells to human herpesviruses infection. *PloS one* 8, e71412 (2013).

29. Soland, M. A., et al. Perivascular stromal cells as a potential reservoir of human cytomegalovirus. *American journal of transplantation: official journal of the American Society of Transplantation and the American Society of Transplant Surgeons* 14, 820-830 (2014).

30. Khatri, M. & Saif, Y. M. Influenza virus infects bone marrow mesenchymal stromal cells in vitro: implications for bone marrow transplantation. *Cell transplantation* 22, 461-468 (2013).

31. Gibellini, D., et al. HIV-1 and recombinant gp120 affect the survival and differentiation of human vessel wall-derived mesenchymal stem cells. *Retrovirology* 8, 40 (2011).

32. Ma, R., et al. Hepatitis B virus infection and replication in human bone marrow mesenchymal stem cells. *Virology journal* 8, 486 (2011).

33. Rodbell, M. Metabolism of isolated fat cells. II. The similar effects of phospholipase C (*Clostridium perfringens* alpha toxin) and of insulin on glucose and amino acid metabolism. *J Biol Chem* 241, 130-139 (1966).

34. Eto, H., et al. Characterization of structure and cellular components of aspirated and excised adipose tissue. *Plast Reconstr Surg* 124, 1087-1097 (2009).

35. Bukh, J., Purcell, R. H. & Miller, R. H. Importance of primer selection for the detection of hepatitis C virus RNA with the polymerase chain reaction assay. *Proc Natl Acad Sci USA* 89, 187-191 (1992).

36. Shimizu, Y. K., Feinstone, S. M., Kohara, M., Purcell, R. H. & Yoshikura, H. Hepatitis C virus: detection of intracellular virus particles by electron microscopy. *Hepatology* 23, 205-209 (1996).

37. Okamoto, H., et al. Typing hepatitis C virus by polymerase chain reaction with type-specific primers: application to clinical surveys and tracing infectious sources. *J Gen Virol* 73 (Pt 3), 673-679 (1992).

38. Toniutto, P., et al. Discordant results from hepatitis C virus genotyping by procedures based on amplification of different genomic regions. *J Clin Microbiol* 34, 2382-2385 (1996).

39. Jopling, C. L., Yi, M., Lancaster, A. M., Lemon, S. M. & Sarnow, P. Modulation of hepatitis C virus RNA abundance by a liver-specific MicroRNA. *Science* 309, 1577-1581 (2005).

40. Al-Sadi, R., et al. Occludin regulates macromolecule flux across the intestinal epithelial tight junction barrier. *Am J Physiol Gastrointest Liver Physiol* 300, G1054-1064 (2011).

41. Jiang, J., et al. Hepatitis C virus attachment mediated by apolipoprotein E binding to cell surface heparan sulfate. *Journal of virology* 86, 7256-7267 (2012).

42. Kato, T., et al. Cell culture and infection system for hepatitis C virus. *Nature protocols* 1, 2334-2339 (2006).

43. Lindenbach, B. D. Complete replication of hepatitis C virus in cell culture. *Science* 309, 623-626 (2005).

44. Lindenbach, B. D., et al. Cell culture-grown hepatitis C virus is infectious in vivo and can be recultured in vitro. *Proc Natl Acad Sci USA* 103, 3805-3809 (2006).

45. Bhogal, R. H., et al. Isolation of primary human hepatocytes from normal and diseased liver tissue: a one hundred liver experience. *PloS one* 6, e18222 (2011).

46. Clark, J. M., Brancati, F. L. & Diehl, A. M. Nonalcoholic fatty liver disease. *Gastroenterology* 122, 1649-1657 (2002).

47. Negro, F. Mechanisms and significance of liver steatosis in hepatitis C virus infection. *World journal of gastroenterology: WJG* 12, 6756-6765 (2006).

48. Adinolfi, L. E., et al. Steatosis accelerates the progression of liver damage of chronic hepatitis C patients and correlates with specific HCV genotype and visceral obesity. *Hepatology* 33, 1358-1364 (2001).

49. Kapadia, S. B. & Chisari, F. V. Hepatitis C virus RNA replication is regulated by host geranylgeranylation and fatty acids. *Proc Natl Acad Sci USA* 102, 2561-2566 (2005).

50. Mankouri, J., et al. Enhanced hepatitis C virus genome replication and lipid accumulation mediated by inhibition of AMP-activated protein kinase. *Proc Natl Acad Sci USA* 107, 11549-11554 (2010).

51. Royer, C., et al. A study of susceptibility of primary human Kupffer cells to hepatitis C virus. *Journal of hepatology* 38, 250-256 (2003).

52. Olson, L. E. & Soriano, P. PDGFRbeta signaling regulates mural cell plasticity and inhibits fat development. *Dev Cell* 20, 815-826 (2011).

53. Pileri, P., et al. Binding of hepatitis C virus to CD81. *Science* 282, 938-941 (1998).

54. Molina, S., et al. Serum-derived hepatitis C virus infection of primary human hepatocytes is tetraspanin CD81 dependent. *Journal of virology* 82, 569-574 (2008).

55. Ploss, A., et al. Human occludin is a hepatitis C virus entry factor required for infection of mouse cells. *Nature* 457, 882-886 (2009).

56. Evans, M. J., et al. Claudin-1 is a hepatitis C virus co-receptor required for a late step in entry. *Nature* 446, 801-805 (2007).

57. Liu, S., et al. Human apolipoprotein E peptides inhibit hepatitis C virus entry by blocking virus binding. *Hepatology* 56, 484-491 (2012).

58. Lupberger, J., et al. EGFR and EphA2 are host factors for hepatitis C virus entry and possible targets for antiviral therapy. *Nature medicine* 17, 589-595 (2011).

59. Kanto, T., et al. Buoyant density of hepatitis C virus recovered from infected hosts: two different features in sucrose equilibrium density-gradient centrifugation related to degree of liver inflammation. *Hepatology* 19, 296-302 (1994).

60. Bartenschlager, R., Frese, M. & Pietschmann, T. Novel insights into hepatitis C virus replication and persistence. *Adv. Virus Res.* 63, 71-180 (2004).

61. Gondeau, C., et al. In vitro infection of primary human hepatocytes by HCV-positive sera: insights on a highly relevant model. *Gut* (2013).

The invention claimed is:

1. A human adipose-derived stem cells (hADSCs)-based system for propagating hepatitis C virus (HCV), which comprises hADSCs, culture medium suitable for culturing hADSCs, and HCV, wherein hADSCs are used to propagate HCV in said culture medium under a condition suitable for replication of HCV and thus HCV replicates in hADSCs.

2. The system of claim 1, wherein the hADSCs are primary cells or passaged cells.

3. The system of claim 1, wherein the HCV is derived from blood, serum, plasma or body fluid of an individual infected with HCV, or is a clinical HCV isolate.

4. The system of claim 1, wherein the HCV is of genotype 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, or any combination thereof.

5. The system of claim 1, wherein the system supports complete replication of HCV.

6. A method for propagating hepatitis C virus (HCV), comprising contacting hADSCs with HCV to propagate HCV in culture medium suitable for culturing hADSCs under a condition suitable for replication of HCV.

7. The method of claim 6, wherein the hADSCs are primary cells or passaged cells.

8. The method of claim 6, wherein the HCV is derived from blood, serum, plasma or body fluid of an individual infected with HCV, or is a clinical HCV isolate.

9. The method of claim 6, wherein the HCV is of genotype 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, or any combination thereof.

10. The method of claim 6, wherein the method supports complete replication of HCV.

11. A method for diagnosing an HCV infection in a subject comprising the steps of:
 a) providing hADSCs,
 b) incubating the hADSCs with a biological sample obtained from the subject in a culture medium suitable for culturing hADSCs,
 c) culturing said hADSCs for a time sufficient for permitting HCV replication, and
 d) detecting the level of HCV replication,
 wherein the detection of an HCV replication is indicative that said subject is infected with HCV.

12. The method according to claim 11 wherein said biological sample is derived from blood, serum, plasma or body fluid.

13. A method for screening an anti-HCV compounds, comprising the steps of:
 a) contacting hADSCs in a culture medium in a first container with HCV in the absence of a candidate compound;
 b) determining the level of HCV in the culture medium in the first container in the absence of the candidate compound;
 c) contacting hADSCs in a culture medium in a second container with HCV in the presence of the candidate compound;
 d) determining the level of HCV in the culture medium in the second container in the presence of the candidate compound;
 e) comparing the level of HCV in the presence of the candidate compound with the level of HCV in the absence of the candidate compound; and
 f) identifying the candidate compound as an anti-HCV compound when the level of HCV in the presence of the candidate compound is lower than level of HCV in the absence of the candidate compound.

14. The method of claim 13, wherein the level of HCV is determined by measuring the HCV titre, the level of an HCV nucleic acid, or the level of an HCV polypeptide.

15. The method of claim 13, wherein the candidate compound is at least one selected from the group consisting of: a chemical compound, a protein, a peptide, a peptidomimetic, an antibody, a nucleic acid, an antisense nucleic acid, an shRNA, a ribozyme, and a small molecule chemical compound.

16. The method of claim 13, wherein the HCV is at least one of the HCV genotypes selected from the group consisting of genotype 1a, 1b, 2a, 2b, 2c, 2d, 3a, 3b, 3c, 3d, 3e, 3f, 4a, 4b, 4c, 4d, 4e, 4f, 4g, 4h, 4i, 4j, 5a and 6a, or any combination thereof.

17. The system of claim 2, wherein the passaged cells are passage 1-15 cells or passage 1-6 cells.

18. The method of claim 7, wherein the passaged cells are passage 1-15 cells or passage 1-6 cells.

\* \* \* \* \*

UNITED STATES PATENT AND TRADEMARK OFFICE
CERTIFICATE OF CORRECTION

PATENT NO. : 10,273,461 B2
APPLICATION NO. : 15/541913
DATED : April 30, 2019
INVENTOR(S) : Chen-Lung Lin Page 1 of 1

It is certified that error appears in the above-identified patent and that said Letters Patent is hereby corrected as shown below:

On the Title Page

Item (56) Reference Cited, OTHER PUBLICATIONS, Page 3, Column 1, last citation in the column, Al-Sadi cite: Please correct "300LG1054-G1064" to read -- 300:G1054-G1064 --

In the Specification

Column 5, Line 36: Please correct "(11)" to read -- (H) --

Column 7, Line 35: Please correct "described$^{12-13}$" to read -- described$^{12,13}$ --

Column 8, Line 16: Please correct "described$^{16-17}$" to read -- described$^{16,17}$ --

Column 10, Line 60: Please correct "reference$^{25-26}$" to read -- reference$^{25,26}$ --

Column 24, Line 21: Please correct "PHI-1" to read -- PHH --

Signed and Sealed this
Thirtieth Day of July, 2019

Andrei Iancu
*Director of the United States Patent and Trademark Office*